(12) United States Patent
Kimoto et al.

(10) Patent No.: US 7,083,962 B2
(45) Date of Patent: Aug. 1, 2006

(54) CARBONYL REDUCTASES, POLYNUCLEOTIDES COMPRISING DNA ENCODING THE SAME, METHODS FOR PRODUCING THE SAME, AND METHODS FOR PRODUCING OPTICALLY ACTIVE ALCOHOL UTILIZING THE SAME

(75) Inventors: Norihiro Kimoto, Ibaraki (JP); Hiroaki Yamamoto, Ibaraki (JP); Takanori Nakajima, Ibaraki (JP)

(73) Assignee: Daicel Chemical Industries Ltd., Osaka (JP)

( * ) Notice: Subject to any disclaimer, the term of this patent is extended or adjusted under 35 U.S.C. 154(b) by 89 days.

(21) Appl. No.: 10/826,081

(22) Filed: Apr. 15, 2004

(65) Prior Publication Data

US 2005/0148057 A1    Jul. 7, 2005

(51) Int. Cl.
| | |
|---|---|
| C12N 9/02 | (2006.01) |
| C12N 1/18 | (2006.01) |
| C12N 15/74 | (2006.01) |
| C12P 21/04 | (2006.01) |
| C07H 21/04 | (2006.01) |

(52) U.S. Cl. .................. 435/189; 435/254.2; 435/69.1; 435/320.1; 536/23.2

(58) Field of Classification Search ................ 435/155, 435/419, 348, 252.3, 254.11, 189, 183, 254.2, 435/320.1, 69.1; 800/13, 295, 317.2, 320.1
See application file for complete search history.

(56) References Cited

U.S. PATENT DOCUMENTS

| | | | |
|---|---|---|---|
| 5,508,461 | A | 4/1996 | Ito et al. |
| 5,629,200 | A | 5/1997 | Furukawa et al. |
| 5,679,557 | A * | 10/1997 | Ito et al. ............... 435/156 |
| 5,811,293 | A | 9/1998 | Furukawa et al. |
| 5,902,900 | A | 5/1999 | Ito et al. |
| 6,114,582 | A | 9/2000 | Furukawa et al. |
| 6,248,573 | B1 | 6/2001 | Ito et al. |
| 6,528,686 | B1 | 3/2003 | Akamatsu et al. |
| 2002/0045233 | A1 | 4/2002 | Hershberger et al. |
| 2003/0143701 | A1 | 7/2003 | Matsuyama et al. |
| 2004/0086993 | A1 | 5/2004 | Kimoto et al. |

FOREIGN PATENT DOCUMENTS

| | | |
|---|---|---|
| DE | 69401306 D1 | 2/1997 |
| DE | 89423179 D1 | 4/1999 |
| EP | 0 627 397 A1 | 12/1994 |
| EP | 0 654 534 A2 | 5/1995 |
| EP | 0 654 534 A3 | 5/1995 |
| EP | 0918090 A2 | 5/1999 |
| EP | 918090 A2 * | 5/1999 |
| JP | 8-89261 A | 4/1996 |
| JP | 8-098697 A | 4/1996 |
| JP | 8-325188 A | 12/1996 |
| WO | WO 99/23242 A1 | 5/1999 |

OTHER PUBLICATIONS

Costello CA, et al. "Purification, characterization, cDNA cloning and expression of a novel ketoreductass from *Zygosaccharomyoes rouxii*." *Eur J Biochem*. Sep. 2000;267(17):5493-501.

Watanabe Y, et al. "Cloning and sequencing of phospholipase B gene from the yeast *Torulespore delbrueckll*." *FEMS Microbiol Lett*. Nov. 15, 1994;124(1):29-34.

* cited by examiner

*Primary Examiner*—Rebecca Prouty
*Assistant Examiner*—Kagnew Gebreyesus
(74) *Attorney, Agent, or Firm*—Lahive & Cockfield, LLP; Elizabeth A. Hanley, Esq.; Jeanne M. DiGiorgio, Esq.

(57) ABSTRACT

An objective of the present invention is to provide methods for efficiently producing (S)-1-(3,4-dimethoxyphenyl)-2-propanol at a high optical purity. Another objective is to provide novel reductases which reduce 3,4-dimethoxyphenylacetone, using NADPH as a coenzyme, to produce (S)-1-(3,4-dimethoxyphenyl)-2-propanol with a high optical purity.

The inventors found that a 3,4-dimethoxyphenylacetone-reducing enzyme present in *Torulaspora delbrueckii* is a novel carbonyl reductase that reduces various carbonyls. This novel enzyme reduces 3,4-dimethoxyphenylacetone in a reduction reaction to produce (S)-1-(3,4-dimethoxyphenyl)-2-propanol with a high optical purity and at a high yield. Furthermore, the inventors isolated a DNA that encodes the present enzyme, and generated a recombinant bacterium which highly expresses the present enzyme. Thus, the present inventors established a simple and highly economical method of obtaining optically active alcohols with a high optical purity and at a high yield.

8 Claims, 14 Drawing Sheets

SEQUENCE LISTING

```
<160> NUMBER OF SEQ ID NOS: 25

<210> SEQ ID NO 1
<211> LENGTH: 1035
<212> TYPE: DNA
<213> ORGANISM: Torulaspora delbrueckii
<220> FEATURE:
<221> NAME/KEY: CDS
<222> LOCATION: (1)..(1032)
<223> OTHER INFORMATION:

<400> SEQUENCE: 1 atg tct att cta gtt tct ggt gct act ggt ttt att gct cta cat gtt      48
Met Ser Ile Leu Val Ser Gly Ala Thr Gly Phe Ile Ala Leu His Val
1               5                  10                  15 gtc agt gat ttg ttg aag cag gat tac aaa gtt att ggt act gtt aga      96
Val Ser Asp Leu Leu Lys Gln Asp Tyr Lys Val Ile Gly Thr Val Arg
            20                  25                  30 tct caa gaa aaa gct gat aaa ttg cgt aag caa ttt ggc aac aat ccc     144
Ser Gln Glu Lys Ala Asp Lys Leu Arg Lys Gln Phe Gly Asn Asn Pro
        35                  40                  45 aat ctt tcc ttt gaa ttg gtt tca gat att gct gct cct gaa gct ttt     192
Asn Leu Ser Phe Glu Leu Val Ser Asp Ile Ala Ala Pro Glu Ala Phe
    50                  55                  60 gac aaa gtc ttt cag aaa cat ggc aag gac atc aaa gtg gtg ttg cac     240
Asp Lys Val Phe Gln Lys His Gly Lys Asp Ile Lys Val Val Leu His
```

| | | | | | | | | | | | | | | | | |
|---|---|---|---|---|---|---|---|---|---|---|---|---|---|---|---|---|
| | | 65 | | | | | 70 | | | | | 75 | | | | 80 |

```
aca gct tct cct ttc act cta gaa acc aca aat tat gag aaa gat ctg      288
Thr Ala Ser Pro Phe Thr Leu Glu Thr Thr Asn Tyr Glu Lys Asp Leu
                85                  90                  95 ttg ctt cca gca gtg aat ggt aca aag agt atc ctg gag tcg att aag      336
Leu Leu Pro Ala Val Asn Gly Thr Lys Ser Ile Leu Glu Ser Ile Lys
            100                 105                 110 aaa tac gct gct gat tct gtc gag aga gta gtc atc aca tcg tct tac      384
Lys Tyr Ala Ala Asp Ser Val Glu Arg Val Val Ile Thr Ser Ser Tyr
        115                 120                 125 gct gcc gtc atg aat gtt tcg aaa gaa ggc gac ggc tca ata gtc tac      432
Ala Ala Val Met Asn Val Ser Lys Glu Gly Asp Gly Ser Ile Val Tyr
    130                 135                 140 act gag aag gat tgg aac cct gcc act tgg gaa aac tgt cag ata gat      480
Thr Glu Lys Asp Trp Asn Pro Ala Thr Trp Glu Asn Cys Gln Ile Asp
145                 150                 155                 160 ggt ttg aat gct tat tgt ggg tcc aag aag cta gca gaa aag gct gca      528
Gly Leu Asn Ala Tyr Cys Gly Ser Lys Lys Leu Ala Glu Lys Ala Ala
                165                 170                 175 tgg gac ttc ttt gaa gat aat aaa aac gtt gtc aag ttc aaa ctg agc      576
Trp Asp Phe Phe Glu Asp Asn Lys Asn Val Val Lys Phe Lys Leu Ser
            180                 185                 190 atg atc aat cct act tac gtt ttc ggg cct cag cta ttt gat gag gac      624
Met Ile Asn Pro Thr Tyr Val Phe Gly Pro Gln Leu Phe Asp Glu Asp
        195                 200                 205 gtg aag gat aaa ttg aat act tcc tgt gag cta att aac tca att ata      672
Val Lys Asp Lys Leu Asn Thr Ser Cys Glu Leu Ile Asn Ser Ile Ile
    210                 215                 220 aag aat aat cct cag gtg gga tat cta tta gag aat att aaa ggt cat      720
Lys Asn Asn Pro Gln Val Gly Tyr Leu Leu Glu Asn Ile Lys Gly His
225                 230                 235                 240 ttc gtt gat gtc aga gat gtt gct aag gct cac ttg gtg gca ttc caa      768
Phe Val Asp Val Arg Asp Val Ala Lys Ala His Leu Val Ala Phe Gln
                245                 250                 255 aag gat gaa gct att gga cag aga ctg ctc acc tca aat ggt cgt ttc      816
Lys Asp Glu Ala Ile Gly Gln Arg Leu Leu Thr Ser Asn Gly Arg Phe
            260                 265                 270 gct tac caa gac ctc gta gat att atc aat gag gat ttc cca caa ttg      864
Ala Tyr Gln Asp Leu Val Asp Ile Ile Asn Glu Asp Phe Pro Gln Leu
        275                 280                 285 aag ggt aag gtc att gta gga aag cca ggt gcc ggt aaa caa ttg tat      912
Lys Gly Lys Val Ile Val Gly Lys Pro Gly Ala Gly Lys Gln Leu Tyr
    290                 295                 300 ggc act ttc cca gac atc aac aac acc aga tcg aag gag att ttg ggc      960
Gly Thr Phe Pro Asp Ile Asn Asn Thr Arg Ser Lys Glu Ile Leu Gly
305                 310                 315                 320 ttc gaa ttc atc tct ctg cat aaa tcc gtc cat gac act gct gct caa     1008
Phe Glu Phe Ile Ser Leu His Lys Ser Val His Asp Thr Ala Ala Gln
                325                 330                 335 gtt ttg aaa aaa gaa ggc aaa ttg taa                                  1035
Val Leu Lys Lys Glu Gly Lys Leu
            340
```

<210> SEQ ID NO 2
<211> LENGTH: 344
<212> TYPE: PRT
<213> ORGANISM: Torulaspora delbrueckii

<400> SEQUENCE: 2

Met Ser Ile Leu Val Ser Gly Ala Thr Gly Phe Ile Ala Leu His Val

```
                1               5                    10                    15
            Val Ser Asp Leu Leu Lys Gln Asp Tyr Lys Val Ile Gly Thr Val Arg
                            20                   25                30

Ser Gln Glu Lys Ala Asp Lys Leu Arg Lys Gln Phe Gly Asn Asn Pro
                            35                   40                45

Asn Leu Ser Phe Glu Leu Val Ser Asp Ile Ala Ala Pro Glu Ala Phe
                        50                   55                60

Asp Lys Val Phe Gln Lys His Gly Lys Asp Ile Lys Val Val Leu His
            65                       70                   75                80

Thr Ala Ser Pro Phe Thr Leu Glu Thr Thr Asn Tyr Glu Lys Asp Leu
                                85                   90                95

Leu Leu Pro Ala Val Asn Gly Thr Lys Ser Ile Leu Glu Ser Ile Lys
                                100                  105               110

Lys Tyr Ala Ala Asp Ser Val Glu Arg Val Val Ile Thr Ser Ser Tyr
                            115                  120                125

Ala Ala Val Met Asn Val Ser Lys Glu Gly Asp Gly Ser Ile Val Tyr
                        130                  135                  140

Thr Glu Lys Asp Trp Asn Pro Ala Thr Trp Glu Asn Cys Gln Ile Asp
            145                      150                  155               160

Gly Leu Asn Ala Tyr Cys Gly Ser Lys Lys Leu Ala Glu Lys Ala Ala
                            165                  170                  175

Trp Asp Phe Phe Glu Asp Asn Lys Asn Val Val Lys Phe Lys Leu Ser
                        180                  185                  190

Met Ile Asn Pro Thr Tyr Val Phe Gly Pro Gln Leu Phe Asp Glu Asp
                        195                  200                  205

Val Lys Asp Lys Leu Asn Thr Ser Cys Glu Leu Ile Asn Ser Ile Ile
            210                      215                  220

Lys Asn Asn Pro Gln Val Gly Tyr Leu Leu Glu Asn Ile Lys Gly His
            225                      230                  235                240

Phe Val Asp Val Arg Asp Val Ala Lys Ala His Leu Val Ala Phe Gln
                            245                  250                  255

Lys Asp Glu Ala Ile Gly Gln Arg Leu Leu Thr Ser Asn Gly Arg Phe
                        260                  265                  270

Ala Tyr Gln Asp Leu Val Asp Ile Ile Asn Glu Asp Phe Pro Gln Leu
                        275                  280                  285

Lys Gly Lys Val Ile Val Gly Lys Pro Gly Ala Gly Lys Gln Leu Tyr
                        290                  295                  300

Gly Thr Phe Pro Asp Ile Asn Asn Thr Arg Ser Lys Glu Ile Leu Gly
            305                      310                  315                320

Phe Glu Phe Ile Ser Leu His Lys Ser Val His Asp Thr Ala Ala Gln
                                325                  330                  335

Val Leu Lys Lys Glu Gly Lys Leu
                        340

<210> SEQ ID NO 3
<211> LENGTH: 10
<212> TYPE: PRT
<213> ORGANISM: Torulaspora delbrueckii

<400> SEQUENCE: 3

Ser Ile Leu Val Ser Gly Ala Thr Gly Phe
1               5                   10

<210> SEQ ID NO 4
<211> LENGTH: 11
```

```
<212> TYPE: PRT
<213> ORGANISM: Torulaspora delbrueckii

<400> SEQUENCE: 4

Asp Leu Leu Leu Pro Ala Val Asn Gly Thr Lys
1               5                   10

<210> SEQ ID NO 5
<211> LENGTH: 32
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (30)..(30)
<223> OTHER INFORMATION: "n" = a, t, c, or g.

<400> SEQUENCE: 5
gtcgaattca tyttrgtbtc hggwgchacn gg                                    32

<210> SEQ ID NO 6
<211> LENGTH: 29
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (27)..(27)
<223> OTHER INFORMATION: "n" = a, t, c, or g.

<400> SEQUENCE: 6
gtcgaattct tdgtwccrtt vacdgcngg                                        29

<210> SEQ ID NO 7
<211> LENGTH: 306
<212> TYPE: DNA
<213> ORGANISM: Torulaspora delbrueckii

<400> SEQUENCE: 7
attttagtgt ccggtgcaac aggttttatt gctctacatg ttgtcagtga tttgttgaag       60
caggattaca aagttattgg tactgttaga tctcaagaaa aagctgataa attgcgtaag      120
caatttggca acaatcccaa tctttccttt gaattggttt cagatattgc tgctcctgaa      180
gcttttgaca aagtctttca gaaacatggc aaggacatca aagtggtgtt gcacacagct      240
tctcctttca ctctagaaac cacaaattat gagaaagatc tgttgcttcc tgccgtcaac      300
ggtact                                                                306

<210> SEQ ID NO 8
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 8
ctaacagtac caataacttt gtaatcctgc                                       30

<210> SEQ ID NO 9
<211> LENGTH: 20
<212> TYPE: DNA
<213> ORGANISM: Artificial
<220> FEATURE:
<223> OTHER INFORMATION: an artificially synthesized primer sequence
```

```
<400> SEQUENCE: 9
cacagcttct cctttcactc                                              20

<210> SEQ ID NO 10
<211> LENGTH: 42
<212> TYPE: DNA
<213> ORGANISM: Artificial
<220> FEATURE:
<223> OTHER INFORMATION: an artificially synthesized primer sequence

<400> SEQUENCE: 10
gtcggatcct atcatgagta ttcttgtttc tggtgctact gg                     42

<210> SEQ ID NO 11
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 11
gtggtttcta gagtgaaagg agaagc                                       26

<210> SEQ ID NO 12
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 12
ctttcactct agaaaccaca aattatgaga aagatc                            36

<210> SEQ ID NO 13
<211> LENGTH: 53
<212> TYPE: DNA
<213> ORGANISM: Artificial
<220> FEATURE:
<223> OTHER INFORMATION: an artificially synthesized primer sequence

<400> SEQUENCE: 13
gacctgcagt atctagatta caatttgcct tcttttttca aaacttgagc agc         53

<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
gagtcatgac tactgatacc actgttttcg                                   30

<210> SEQ ID NO 15
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 15
gagtctagat tatgcttcat tttgaacttc taacatttgc                        40

<210> SEQ ID NO 16
```

<211> LENGTH: 1044
<212> TYPE: DNA
<213> ORGANISM: Saccharomyces cerevisiae
<220> FEATURE:
<221> NAME/KEY: CDS
<222> LOCATION: (1)..(1041)
<223> OTHER INFORMATION:

<400> SEQUENCE: 16

| | | | | | | | | | | | | | | | | |
|---|---|---|---|---|---|---|---|---|---|---|---|---|---|---|---|---|
| atg | act | act | gat | acc | act | gtt | ttc | gtt | tct | ggc | gca | acc | ggt | ttc | att | 48 |
| Met | Thr | Thr | Asp | Thr | Thr | Val | Phe | Val | Ser | Gly | Ala | Thr | Gly | Phe | Ile | |
| 1 | | | | 5 | | | | | 10 | | | | | 15 | | |
| gct | cta | cac | att | atg | aac | gat | ctg | ttg | aaa | gct | ggc | tat | aca | gtc | atc | 96 |
| Ala | Leu | His | Ile | Met | Asn | Asp | Leu | Leu | Lys | Ala | Gly | Tyr | Thr | Val | Ile | |
| | | | 20 | | | | | 25 | | | | | 30 | | | |
| ggc | tca | ggt | aga | tct | caa | gaa | aaa | aat | gat | ggc | ttg | ctc | aaa | aaa | ttt | 144 |
| Gly | Ser | Gly | Arg | Ser | Gln | Glu | Lys | Asn | Asp | Gly | Leu | Leu | Lys | Lys | Phe | |
| | | 35 | | | | | 40 | | | | | 45 | | | | |
| aat | aac | aat | ccc | aaa | cta | tcg | atg | gaa | att | gtg | gaa | gat | att | gct | gct | 192 |
| Asn | Asn | Asn | Pro | Lys | Leu | Ser | Met | Glu | Ile | Val | Glu | Asp | Ile | Ala | Ala | |
| | 50 | | | | | 55 | | | | | 60 | | | | | |
| cca | aac | gcc | ttt | gat | gaa | gtt | ttc | aaa | aaa | cat | ggt | aag | gaa | att | aag | 240 |
| Pro | Asn | Ala | Phe | Asp | Glu | Val | Phe | Lys | Lys | His | Gly | Lys | Glu | Ile | Lys | |
| 65 | | | | 70 | | | | | 75 | | | | | 80 | | |
| att | gtg | cta | cac | act | gcc | tcc | cca | ttc | cat | ttt | gaa | act | acc | aat | ttt | 288 |
| Ile | Val | Leu | His | Thr | Ala | Ser | Pro | Phe | His | Phe | Glu | Thr | Thr | Asn | Phe | |
| | | | 85 | | | | | 90 | | | | | 95 | | | |
| gaa | aag | gat | tta | cta | acc | cct | gca | gtg | aac | ggt | aca | aaa | tct | atc | ttg | 336 |
| Glu | Lys | Asp | Leu | Leu | Thr | Pro | Ala | Val | Asn | Gly | Thr | Lys | Ser | Ile | Leu | |
| | | 100 | | | | | 105 | | | | | 110 | | | | |
| gaa | gcg | att | aaa | aaa | tat | gct | gca | gac | act | gtt | gaa | aaa | gtt | att | gtt | 384 |
| Glu | Ala | Ile | Lys | Lys | Tyr | Ala | Ala | Asp | Thr | Val | Glu | Lys | Val | Ile | Val | |
| | | 115 | | | | | 120 | | | | | 125 | | | | |
| act | tcg | tct | act | gct | gct | ctg | gtg | aca | cct | aca | gac | atg | aac | aaa | gga | 432 |
| Thr | Ser | Ser | Thr | Ala | Ala | Leu | Val | Thr | Pro | Thr | Asp | Met | Asn | Lys | Gly | |
| | 130 | | | | | 135 | | | | | 140 | | | | | |
| gat | ttg | gtg | atc | acg | gag | gag | agt | tgg | aat | aag | gat | aca | tgg | gac | agt | 480 |
| Asp | Leu | Val | Ile | Thr | Glu | Glu | Ser | Trp | Asn | Lys | Asp | Thr | Trp | Asp | Ser | |
| 145 | | | | 150 | | | | | 155 | | | | | 160 | | |
| tgt | caa | gcc | aac | gcc | gtt | gcc | gca | tat | tgt | ggc | tcg | aaa | aag | ttt | gct | 528 |
| Cys | Gln | Ala | Asn | Ala | Val | Ala | Ala | Tyr | Cys | Gly | Ser | Lys | Lys | Phe | Ala | |
| | | | 165 | | | | | 170 | | | | | 175 | | | |
| gaa | aaa | act | gct | tgg | gaa | ttt | ctt | aaa | gaa | aac | aag | tct | agt | gtc | aaa | 576 |
| Glu | Lys | Thr | Ala | Trp | Glu | Phe | Leu | Lys | Glu | Asn | Lys | Ser | Ser | Val | Lys | |
| | | 180 | | | | | 185 | | | | | 190 | | | | |
| ttc | aca | cta | tcc | act | atc | aat | ccg | gga | ttc | gtt | ttt | ggt | cct | caa | atg | 624 |
| Phe | Thr | Leu | Ser | Thr | Ile | Asn | Pro | Gly | Phe | Val | Phe | Gly | Pro | Gln | Met | |
| | | 195 | | | | | 200 | | | | | 205 | | | | |
| ttt | gca | gat | tcg | cta | aaa | cat | ggc | ata | aat | acc | tcc | tca | ggg | atc | gta | 672 |
| Phe | Ala | Asp | Ser | Leu | Lys | His | Gly | Ile | Asn | Thr | Ser | Ser | Gly | Ile | Val | |
| | 210 | | | | | 215 | | | | | 220 | | | | | |
| tct | gag | tta | att | cat | tcc | aag | gta | ggt | gga | gaa | ttt | tat | aat | tac | tgt | 720 |
| Ser | Glu | Leu | Ile | His | Ser | Lys | Val | Gly | Gly | Glu | Phe | Tyr | Asn | Tyr | Cys | |
| 225 | | | | 230 | | | | | 235 | | | | | 240 | | |
| ggc | cca | ttt | att | gac | gtg | cgt | gac | gtt | tct | aaa | gcc | cac | cta | gtt | gca | 768 |
| Gly | Pro | Phe | Ile | Asp | Val | Arg | Asp | Val | Ser | Lys | Ala | His | Leu | Val | Ala | |
| | | | 245 | | | | | 250 | | | | | 255 | | | |
| att | gaa | aaa | cca | gaa | tgt | acc | ggc | caa | aga | tta | gta | ttg | agt | gaa | ggt | 816 |
| Ile | Glu | Lys | Pro | Glu | Cys | Thr | Gly | Gln | Arg | Leu | Val | Leu | Ser | Glu | Gly | |
| | | 260 | | | | | 265 | | | | | 270 | | | | |
| tta | ttc | tgc | tgt | caa | gaa | atc | gtt | gac | atc | ttg | aac | gag | gaa | ttc | cct | 864 |

```
                Leu Phe Cys Cys Gln Glu Ile Val Asp Ile Leu Asn Glu Glu Phe Pro
                            275                 280                 285 caa tta aag ggc aag ata gct aca ggt gaa cct gcg acc ggt cca agc              912
Gln Leu Lys Gly Lys Ile Ala Thr Gly Glu Pro Ala Thr Gly Pro Ser
    290                 295                 300 ttt tta gaa aaa aac tct tgc aag ttt gac aat tct aag aca aaa aaa              960
Phe Leu Glu Lys Asn Ser Cys Lys Phe Asp Asn Ser Lys Thr Lys Lys
305                 310                 315                 320 cta ctg gga ttc cag ttt tac aat tta aag gat tgc ata gtt gac acc             1008
Leu Leu Gly Phe Gln Phe Tyr Asn Leu Lys Asp Cys Ile Val Asp Thr
                325                 330                 335 gcg gcg caa atg tta gaa gtt caa aat gaa gcc taa                             1044
Ala Ala Gln Met Leu Glu Val Gln Asn Glu Ala
            340                 345
```

<210> SEQ ID NO 17
<211> LENGTH: 347
<212> TYPE: PRT
<213> ORGANISM: Saccharomyces cerevisiae

<400> SEQUENCE: 17

```
Met Thr Thr Asp Thr Thr Val Phe Val Ser Gly Ala Thr Gly Phe Ile
1               5                   10                  15

Ala Leu His Ile Met Asn Asp Leu Leu Lys Ala Gly Tyr Thr Val Ile
            20                  25                  30

Gly Ser Gly Arg Ser Gln Glu Lys Asn Asp Gly Leu Leu Lys Lys Phe
        35                  40                  45

Asn Asn Asn Pro Lys Leu Ser Met Glu Ile Val Glu Asp Ile Ala Ala
    50                  55                  60

Pro Asn Ala Phe Asp Glu Val Phe Lys Lys His Gly Lys Glu Ile Lys
65                  70                  75                  80

Ile Val Leu His Thr Ala Ser Pro Phe His Phe Glu Thr Thr Asn Phe
                85                  90                  95

Glu Lys Asp Leu Leu Thr Pro Ala Val Asn Gly Thr Lys Ser Ile Leu
            100                 105                 110

Glu Ala Ile Lys Lys Tyr Ala Ala Asp Thr Val Glu Lys Val Ile Val
        115                 120                 125

Thr Ser Ser Thr Ala Ala Leu Val Thr Pro Thr Asp Met Asn Lys Gly
    130                 135                 140

Asp Leu Val Ile Thr Glu Glu Ser Trp Asn Lys Asp Thr Trp Asp Ser
145                 150                 155                 160

Cys Gln Ala Asn Ala Val Ala Ala Tyr Cys Gly Ser Lys Lys Phe Ala
                165                 170                 175

Glu Lys Thr Ala Trp Glu Phe Leu Lys Glu Asn Lys Ser Ser Val Lys
            180                 185                 190

Phe Thr Leu Ser Thr Ile Asn Pro Gly Phe Val Phe Gly Pro Gln Met
        195                 200                 205

Phe Ala Asp Ser Leu Lys His Gly Ile Asn Thr Ser Ser Gly Ile Val
    210                 215                 220

Ser Glu Leu Ile His Ser Lys Val Gly Gly Glu Phe Tyr Asn Tyr Cys
225                 230                 235                 240

Gly Pro Phe Ile Asp Val Arg Asp Val Ser Lys Ala His Leu Val Ala
                245                 250                 255

Ile Glu Lys Pro Glu Cys Thr Gly Gln Arg Leu Val Leu Ser Glu Gly
            260                 265                 270

Leu Phe Cys Cys Gln Glu Ile Val Asp Ile Leu Asn Glu Glu Phe Pro
```

```
              275                 280                 285
Gln Leu Lys Gly Lys Ile Ala Thr Gly Glu Pro Ala Thr Gly Pro Ser
        290                 295                 300

Phe Leu Glu Lys Asn Ser Cys Lys Phe Asp Asn Ser Lys Thr Lys Lys
305                 310                 315                 320

Leu Leu Gly Phe Gln Phe Tyr Asn Leu Lys Asp Cys Ile Val Asp Thr
                325                 330                 335

Ala Ala Gln Met Leu Glu Val Gln Asn Glu Ala
            340                 345

<210> SEQ ID NO 18
<211> LENGTH: 44
<212> TYPE: DNA
<213> ORGANISM: Artificial
<220> FEATURE:
<223> OTHER INFORMATION: an artificially synthesized primer sequence

<400> SEQUENCE: 18
cgagtcatga ctactgagaa aaccgttgtg tttgtttctg gtgc                      44

<210> SEQ ID NO 19
<211> LENGTH: 44
<212> TYPE: DNA
<213> ORGANISM: Artificial
<220> FEATURE:
<223> OTHER INFORMATION: an artificially synthesized primer sequence

<400> SEQUENCE: 19
cgagctagca ttagctttta ctttgaactt ctagtaattg cgag                      44

<210> SEQ ID NO 20
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1044)
<223> OTHER INFORMATION:

<400> SEQUENCE: 20 atg act act gaa aaa acc gtt gtt ttt gtt tct ggt gct act ggt ttc        48
Met Thr Thr Glu Lys Thr Val Val Phe Val Ser Gly Ala Thr Gly Phe
1               5                   10                  15 att gct cta cac gta gtg gac gat tta tta aaa act ggt tac aag gtc        96
Ile Ala Leu His Val Val Asp Asp Leu Leu Lys Thr Gly Tyr Lys Val
            20                  25                  30 atc ggt tcg ggt agg tcc caa gaa aag aat gat gga ttg ctg aaa aaa       144
Ile Gly Ser Gly Arg Ser Gln Glu Lys Asn Asp Gly Leu Leu Lys Lys
        35                  40                  45 ttt aag agc aat ccc aac ctt tca atg gag att gtc gaa gac att gct       192
Phe Lys Ser Asn Pro Asn Leu Ser Met Glu Ile Val Glu Asp Ile Ala
    50                  55                  60 gct cca aac gct ttt gac aaa gtt ttt caa aag cac ggc aaa gag atc       240
Ala Pro Asn Ala Phe Asp Lys Val Phe Gln Lys His Gly Lys Glu Ile
65                  70                  75                  80 aag gtt gtc ttg cac ata gct tct ccg gtt cac ttc aac acc act gat       288
Lys Val Val Leu His Ile Ala Ser Pro Val His Phe Asn Thr Thr Asp
                85                  90                  95 ttc gaa aag gat ctg cta att cct gct gtg aat ggt acc aag tcc att       336
Phe Glu Lys Asp Leu Leu Ile Pro Ala Val Asn Gly Thr Lys Ser Ile
            100                 105                 110 cta gaa gca atc aaa aat tat gcc gca gac aca gtc gaa aaa gtc gtt       384
```

-continued

```
Leu Glu Ala Ile Lys Asn Tyr Ala Ala Asp Thr Val Glu Lys Val Val
        115                 120                 125 att act tct tct gtt gct gcc ctt gca tct ccc gga gat atg aag gac      432
Ile Thr Ser Ser Val Ala Ala Leu Ala Ser Pro Gly Asp Met Lys Asp
    130                 135                 140 act agt ttc gtt gtc aat gag gaa agt tgg aac aaa gat act tgg gaa      480
Thr Ser Phe Val Val Asn Glu Glu Ser Trp Asn Lys Asp Thr Trp Glu
145                 150                 155                 160 agt tgt caa gct aac gcg gtt tcc gca tac tgt ggt tcc aag aaa ttt      528
Ser Cys Gln Ala Asn Ala Val Ser Ala Tyr Cys Gly Ser Lys Lys Phe
                165                 170                 175 gct gaa aaa act gct tgg gat ttt ctc gag gaa aac caa tca agc atc      576
Ala Glu Lys Thr Ala Trp Asp Phe Leu Glu Glu Asn Gln Ser Ser Ile
            180                 185                 190 aaa ttt acg cta tca acc atc aac cca gga ttt gtt ttt ggc cct cag      624
Lys Phe Thr Leu Ser Thr Ile Asn Pro Gly Phe Val Phe Gly Pro Gln
        195                 200                 205 cta ttt gcc gac tct ctt aga aat gga ata aat agc tct tca gcc att      672
Leu Phe Ala Asp Ser Leu Arg Asn Gly Ile Asn Ser Ser Ser Ala Ile
    210                 215                 220 att gcc aat ttg gtt agt tat aaa tta ggc gac aat ttt tat aat tac      720
Ile Ala Asn Leu Val Ser Tyr Lys Leu Gly Asp Asn Phe Tyr Asn Tyr
225                 230                 235                 240 agt ggt cct ttt att gac gtt cgc gat gtt tca aaa gct cat tta ctt      768
Ser Gly Pro Phe Ile Asp Val Arg Asp Val Ser Lys Ala His Leu Leu
                245                 250                 255 gca ttt gag aaa ccc gaa tgc gct ggc caa aga cta ttc tta tgt gaa      816
Ala Phe Glu Lys Pro Glu Cys Ala Gly Gln Arg Leu Phe Leu Cys Glu
            260                 265                 270 gat atg ttt tgc tct caa gaa gcg ctg gat atc ttg aat gag gaa ttt      864
Asp Met Phe Cys Ser Gln Glu Ala Leu Asp Ile Leu Asn Glu Glu Phe
        275                 280                 285 cca cag tta aaa ggc aag ata gca act ggc gaa cct ggt agc ggc tca      912
Pro Gln Leu Lys Gly Lys Ile Ala Thr Gly Glu Pro Gly Ser Gly Ser
    290                 295                 300 acc ttt ttg aca aaa aac tgc tgc aag tgc gac aac cgc aaa acc aaa      960
Thr Phe Leu Thr Lys Asn Cys Cys Lys Cys Asp Asn Arg Lys Thr Lys
305                 310                 315                 320 aat tta tta gga ttc caa ttt aat aag ttc aga gat tgc att gtc gat     1008
Asn Leu Leu Gly Phe Gln Phe Asn Lys Phe Arg Asp Cys Ile Val Asp
                325                 330                 335 act gcc tcg caa tta cta gaa gtt caa agt aaa agc taa                 1047
Thr Ala Ser Gln Leu Leu Glu Val Gln Ser Lys Ser
            340                 345
```

<210> SEQ ID NO 21
<211> LENGTH: 348
<212> TYPE: PRT
<213> ORGANISM: Saccharomyces cerevisiae

<400> SEQUENCE: 21

```
Met Thr Thr Glu Lys Thr Val Val Phe Val Ser Gly Ala Thr Gly Phe
1               5                   10                  15

Ile Ala Leu His Val Asp Asp Leu Leu Lys Thr Gly Tyr Lys Val
            20                  25                  30

Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
    50                  55                  60
```

-continued

```
Ala Pro Asn Ala Phe Asp Lys Val Phe Gln Lys His Gly Lys Glu Ile
 65                  70                  75                  80

Lys Val Val Leu His Ile Ala Ser Pro Val His Phe Asn Thr Thr Asp
                 85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175

Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285

Pro Gln Leu Lys Gly Lys Ile Ala Thr Gly Glu Pro Gly Ser Gly Ser
290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
            340                 345
```

<210> SEQ ID NO 22
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 22
gcaacatgtc taatacagtt ctagtttctg         30

<210> SEQ ID NO 23
<211> LENGTH: 41
<212> TYPE: DNA
<213> ORGANISM: Artificial
<220> FEATURE:
<223> OTHER INFORMATION: an artificially synthesized primer sequence

<400> SEQUENCE: 23
ggttctagat tataaacggt tctccttctt caaaatttgg g         41

```
<210> SEQ ID NO 24
<211> LENGTH: 1035
<212> TYPE: DNA
<213> ORGANISM: Saccharomyces cerevisiae
<220> FEATURE:
<221> NAME/KEY: CDS
<222> LOCATION: (1)..(1032)
<223> OTHER INFORMATION:

<400> SEQUENCE: 24 atg tct aat aca gtt cta gtt tct ggc gct tca ggt ttt att gcc ttg      48
Met Ser Asn Thr Val Leu Val Ser Gly Ala Ser Gly Phe Ile Ala Leu
1               5                   10                  15 cat atc ctg tca caa ttg tta aaa caa gat tat aag gtt att gga act      96
His Ile Leu Ser Gln Leu Leu Lys Gln Asp Tyr Lys Val Ile Gly Thr
            20                  25                  30 gtg aga tcc cat gaa aaa gaa gca aaa ttg cta aga caa ttt caa cat     144
Val Arg Ser His Glu Lys Glu Ala Lys Leu Leu Arg Gln Phe Gln His
        35                  40                  45 aac cct aat tta act tta gaa att gtt ccg gac att tct cat cca aat     192
Asn Pro Asn Leu Thr Leu Glu Ile Val Pro Asp Ile Ser His Pro Asn
    50                  55                  60 gct ttc gat aag gtt ctg cag aaa cgt gga cgt gag att agg tat gtt     240
Ala Phe Asp Lys Val Leu Gln Lys Arg Gly Arg Glu Ile Arg Tyr Val
65                  70                  75                  80 cta cac acg gcc tct cct ttt cat tat gat act acc gaa tat gaa aaa     288
Leu His Thr Ala Ser Pro Phe His Tyr Asp Thr Thr Glu Tyr Glu Lys
                85                  90                  95 gac tta ttg att ccc gcg tta gaa ggt aca aaa aac atc cta aat tct     336
Asp Leu Leu Ile Pro Ala Leu Glu Gly Thr Lys Asn Ile Leu Asn Ser
            100                 105                 110 atc aag aaa tat gca gca gac act gta gag cgt gtt gtt gtg act tct     384
Ile Lys Lys Tyr Ala Ala Asp Thr Val Glu Arg Val Val Val Thr Ser
        115                 120                 125 tct tgt act gct att ata acc ctt gca aag atg gac gat ccc agt gtg     432
Ser Cys Thr Ala Ile Ile Thr Leu Ala Lys Met Asp Asp Pro Ser Val
    130                 135                 140 gtt ttt aca gaa gag agt tgg aac gaa gca acc tgg gaa agc tgt caa     480
Val Phe Thr Glu Glu Ser Trp Asn Glu Ala Thr Trp Glu Ser Cys Gln
145                 150                 155                 160 att gat ggg ata aat gct tac ttt gca tcc aag aag ttt gct gaa aag     528
Ile Asp Gly Ile Asn Ala Tyr Phe Ala Ser Lys Lys Phe Ala Glu Lys
                165                 170                 175 gct gcc tgg gag ttc aca aaa gag aat gaa gat cac atc aaa ttc aaa     576
Ala Ala Trp Glu Phe Thr Lys Glu Asn Glu Asp His Ile Lys Phe Lys
            180                 185                 190 cta aca aca gtc aac cct tct ctt ctt ttt ggt cct caa ctt ttc gat     624
Leu Thr Thr Val Asn Pro Ser Leu Leu Phe Gly Pro Gln Leu Phe Asp
        195                 200                 205 gaa gat gtg cat ggc cat ttg aat act tct tgc gaa atg atc aat ggc     672
Glu Asp Val His Gly His Leu Asn Thr Ser Cys Glu Met Ile Asn Gly
    210                 215                 220 cta att cat acc cca gta aat gcc agt gtt cct gat ttt cat tcc att     720
Leu Ile His Thr Pro Val Asn Ala Ser Val Pro Asp Phe His Ser Ile
225                 230                 235                 240 ttt att gat gta agg gat gtg gcc cta gct cat ctg tat gct ttc cag     768
Phe Ile Asp Val Arg Asp Val Ala Leu Ala His Leu Tyr Ala Phe Gln
                245                 250                 255 aag gaa aat acc gcg ggt aaa aga tta gtg gta act aac ggt aaa ttt     816
Lys Glu Asn Thr Ala Gly Lys Arg Leu Val Val Thr Asn Gly Lys Phe
            260                 265                 270
```

-continued

```
gga aac caa gat atc ctg gat att ttg aac gaa gat ttt cca caa tta        864
Gly Asn Gln Asp Ile Leu Asp Ile Leu Asn Glu Asp Phe Pro Gln Leu
        275                 280                 285 aga ggt ctc att cct ttg ggt aag cct ggc aca ggt gat caa gtc att        912
Arg Gly Leu Ile Pro Leu Gly Lys Pro Gly Thr Gly Asp Gln Val Ile
290                 295                 300 gac cgc ggt tca act aca gat aat agt gca acg agg aaa ata ctt ggc        960
Asp Arg Gly Ser Thr Thr Asp Asn Ser Ala Thr Arg Lys Ile Leu Gly
305                 310                 315                 320 ttt gag ttc aga agt tta cac gaa agt gtc cat gat act gct gcc caa       1008
Phe Glu Phe Arg Ser Leu His Glu Ser Val His Asp Thr Ala Ala Gln
                325                 330                 335 att ttg aag aag gag aac aga tta tga                                   1035
Ile Leu Lys Lys Glu Asn Arg Leu
                340
```

<210> SEQ ID NO 25
<211> LENGTH: 344
<212> TYPE: PRT
<213> ORGANISM: Saccharomyces cerevisiae

<400> SEQUENCE: 25

```
Met Ser Asn Thr Val Leu Val Ser Gly Ala Ser Gly Phe Ile Ala Leu
1               5                   10                  15

His Ile Leu Ser Gln Leu Leu Lys Gln Asp Tyr Lys Val Ile Gly Thr
            20                  25                  30

Val Arg Ser His Glu Lys Glu Ala Lys Leu Leu Arg Gln Phe Gln His
        35                  40                  45

Asn Pro Asn Leu Thr Leu Glu Ile Val Pro Asp Ile Ser His Pro Asn
    50                  55                  60

Ala Phe Asp Lys Val Leu Gln Lys Arg Gly Arg Glu Ile Arg Tyr Val
65                  70                  75                  80

Leu His Thr Ala Ser Pro Phe His Tyr Asp Thr Thr Glu Tyr Glu Lys
                85                  90                  95

Asp Leu Leu Ile Pro Ala Leu Glu Gly Thr Lys Asn Ile Leu Asn Ser
            100                 105                 110

Ile Lys Lys Tyr Ala Ala Asp Thr Val Glu Arg Val Val Val Thr Ser
        115                 120                 125

Ser Cys Thr Ala Ile Ile Thr Leu Ala Lys Met Asp Asp Pro Ser Val
    130                 135                 140

Val Phe Thr Glu Glu Ser Trp Asn Glu Ala Thr Trp Glu Ser Cys Gln
145                 150                 155                 160

Ile Asp Gly Ile Asn Ala Tyr Phe Ala Ser Lys Lys Phe Ala Glu Lys
                165                 170                 175

Ala Ala Trp Glu Phe Thr Lys Glu Asn Glu Asp His Ile Lys Phe Lys
            180                 185                 190

Leu Thr Thr Val Asn Pro Ser Leu Leu Phe Gly Pro Gln Leu Phe Asp
        195                 200                 205

Glu Asp Val His Gly His Leu Asn Thr Ser Cys Glu Met Ile Asn Gly
    210                 215                 220

Leu Ile His Thr Pro Val Asn Ala Ser Val Pro Asp Phe His Ser Ile
225                 230                 235                 240

Phe Ile Asp Val Arg Asp Val Ala Leu Ala His Leu Tyr Ala Phe Gln
                245                 250                 255

Lys Glu Asn Thr Ala Gly Lys Arg Leu Val Val Thr Asn Gly Lys Phe
            260                 265                 270
```

```
-continued

Gly Asn Gln Asp Ile Leu Asp Ile Leu Asn Glu Asp Phe Pro Gln Leu
    275                 280                 285

Arg Gly Leu Ile Pro Leu Gly Lys Pro Gly Thr Gly Asp Gln Val Ile
    290                 295                 300

Asp Arg Gly Ser Thr Thr Asp Asn Ser Ala Thr Arg Lys Ile Leu Gly
305                 310                 315                 320

Phe Glu Phe Arg Ser Leu His Glu Ser Val His Asp Thr Ala Ala Gln
            325                 330                 335

Ile Leu Lys Lys Glu Asn Arg Leu
            340
```

US 7,083,962 B2

CARBONYL REDUCTASES, POLYNUCLEOTIDES COMPRISING DNA ENCODING THE SAME, METHODS FOR PRODUCING THE SAME, AND METHODS FOR PRODUCING OPTICALLY ACTIVE ALCOHOL UTILIZING THE SAME

FIELD OF THE INVENTION

The present invention relates to novel carbonyl reductases that are dependent on reduced β-nicotinamide adenine dinucleotide phosphate (hereinafter, also referred to as NADPH). The present invention also relates to polynucleotides encoding these enzyme proteins, methods for producing the enzymes, and methods for producing (S)-1-(3,4-dimethoxyphenyl)-2-propanol using the enzymes.

BACKGROUND OF THE INVENTION (S)-1-(3,4-dimethoxyphenyl)-2-propanol was conventionally produced by reducing 3,4-dimethoxyphenylacetone using microorganisms (see Unexamined Published Japanese Patent Application No. (JP-A) Hei 8-325188 and JP-A Hei 8-89261). However, these methods are not very productive, and only yield the product in a concentration of 1% or less. For this reason, there was a need in the art to establish a simple and highly economical method of obtaining (S)-1-(3,4-dimethoxyphenyl)-2-propanol with a high optical purity and at a high reaction yield.

SUMMARY OF THE INVENTION

An objective of the present invention is to provide methods for efficiently producing (S)-1-(3,4-dimethoxyphenyl)-2-propanol with a high optical purity.

Another objective of the present invention is to provide novel enzymes that reduce 3,4-dimethoxyphenylacetone by utilizing NADPH as a coenzyme to produce (S)-1-(3,4-dimethoxyphenyl)-2-propanol with a high optical purity. A further objective of the present invention is to isolate DNA that encode enzymes comprising the desired property, and to obtain the DNA as recombinant DNA. In addition, a further objective is to provide methods for producing (S)-1-(3,4-dimethoxyphenyl)-2-propanol using this recombinant.

In the search for a simple and highly economical method for producing (S)-1-(3,4-dimethoxyphenyl)-2-propanol with a high optical purity, the present inventors focused on a method of over expressing, in a heterologous microorganism, an enzyme that stereo-selectively reduces 3,4-dimethoxyphenylacetone to produce (S)-1-(3,4-dimethoxyphenyl)-2-propanol, and then using the resulting highly active genetically recombinant bacterium to efficiently produce (S)-1-(3,4-dimethoxyphenyl)-2-propanol from 3,4-dimethoxyphenylacetone. The present inventors found that $Torulaspora\ delbrueckii$ had a high reaction yield and high stereoselectivity. They then conducted studies on enzymes in this bacterial strain, which are involved in the reduction of 3,4-dimethoxyphenylacetone. Electrophoresis of a cell-free extract of this bacterial strain showed that an enzyme could be purified to a single electrophoretic band, thus clarifying some of the enzyme's basic properties. As a result, this enzyme was found to be a novel carbonyl reductase that reduces various carbonyls. In addition, the present enzyme reduced 3,4-dimethoxyphenylacetone to produce (S)-1-(3,4-dimethoxyphenyl)-2-propanol with a high optical purity and at a high yield.

Furthermore, the present inventors isolated a DNA encoding the present enzyme, and produced a recombinant bacterium which overexpresses this enzyme, thus completing the present invention. That is, the present invention relates to carbonyl reductases, polynucleotide comprising DNA that encode these enzymes, methods for producing these enzymes, and the use of these enzymes, as set out below.

In the art it is well known that the enzyme 'phenylacetoaldehyde reductase' reduces 3,4-dimethoxyphenylacetone (Eur. J. Biochem., 269, 2394–2402 (2002)). This enzyme reduces ketones in an NADH-dependent manner, and comprises the activity of dehydrogenating secondary alcohols also in an NADH-dependent manner. Thus, it has properties different from the carbonyl reductases of the present invention.

In addition, it is also well known in the art that the enzyme ketoreductase (Eur. J. Biochem., 267, 5493–5501 (2000)), produced by $Zygosaccharomyces\ rouxii$, can reduce 3,4-methylenedioxyphenylacetone, which has a structure similar to $Zygosaccharomyces\ rouxii$ 3,4-dimethoxyphenylacetone. However, there are no reports of its stereoselectivity or activity towards 3,4-dimethoxyphenylacetone. Furthermore, the properties of this enzyme, such as a molecular weight of 42,000 in SDS-PAGE, an optimal pH of 6.6 to 6.8, and an optimal temperature of 37 to 39° C., are different to those of the carbonyl reductases of the present invention.

Furthermore, using the amino acid sequence described in SEQ ID NO: 2, the present inventors performed a SWISS-PROT homology search using a BLAST program. They found proteins homologous to the carbonyl reductases of the present invention. Specifically, genome analysis of $Saccharomyces\ cerevisiae$ resulted in four kinds of predicted ORFs, designated as YGL157w, YGL039w, YDR541c, and YOL151w, respectively. Of these, the functions of proteins encoded by YGL157w, YGL039w, and YDR541c were unknown. YOL151w's activity in reducing various carbonyl compounds had been measured in J. Am. Chem. Soc., 123(8), 1547–1555(2001), but there were no reports of its activity on 3,4-dimethoxyphenylacetone.

Thus, the present invention relates to novel carbonyl reductases, polynucleotides encoding these enzymes, methods for producing these enzymes, methods for producing an optically active alcohol utilizing these enzymes, and uses thereof, as set out below. More specifically, the present invention provides:

[1] a carbonyl reductase comprising the physicochemical properties as shown in (1) and (2), (1) action reduces ketones to produce an optically active alcohol, by utilizing reduced β-nicotinamide adenine dinucleotide phosphate as a coenzyme, (2) substrate specificity (a) utilizes reduced β-nicotinamide adenine dinucleotide phosphate as a coenzyme in the reduction reaction, (b) reduces 3,4-dimethoxyphenylacetone to produce (s)-1-(3,4-dimethoxyphenyl)-2-propanol, (c) comprises the activity of reducing 3,4-dimethoxyphenylacetone, but lacks the activity of oxidizing (S)-1-(3,4-dimethoxyphenyl)-2-propanol;

[2] the carbonyl reductase of [1], which additionally comprises the physicochemical properties of (3) and (4), (3) optimal pH pH 5.5 to 6.5, (4) molecular weight a molecular weight, determined via sodium dodecylsulfate-polyacrylamide gel electrophoresis (SDS-PAGE) and gel filtration, of about 38,000;

[3] the carbonyl reductase of [1], which is produced by a microorganism belonging to the genus *Torulaspora*;

[4] the carbonyl reductase of [3], wherein the microorganism belonging to the genus *Torulaspora* is *Torulaspora delbrueckii*;

[5] a polynucleotide of the following (a) or (b), (a) a polynucleotide comprising the nucleotide sequence of SEQ ID NO: 1

(b) a polynucleotide encoding a protein comprising the amino acid sequence of SEQ ID NO: 2;

[6] a polynucleotide encoding a protein comprising the physicochemical properties of (1) and (2) in [1], wherein said polynucleotide is any one of the following (c) to (e), (c) a polynucleotide encoding a protein comprising an amino acid sequence in which one or more amino acid(s) in the amino acid sequence of SEQ ID NO: 2 has been substituted, deleted, inserted, and/or added, (d) a polynucleotide which hybridizes with a DNA comprising the nucleotide sequence of SEQ ID NO: 1 under stringent conditions, (e) a polynucleotide encoding an amino acid sequence comprising 70% or more homology to the amino acid sequence of SEQ ID NO: 2;

[7] a protein encoded by the polynucleotide of [5] or [6];

[8] a recombinant vector, which comprises the polynucleotide of [5] or [6];

[9] the recombinant vector of [8], which further comprises a dehydrogenase gene for regenerating a coenzyme;

[10] a transformant, which is transformed with the polynucleotide of [5] or [6], or the recombinant vector of [8] or [9];

[11] a carbonyl reducing agent comprising a protein comprising the physiochemical properties of (1) and (2) in [1], and comprising the function of producing at least 80% ee or more (S)-1-(3,4-dimethoxyphenyl)-2-propanol, wherein said protein is encoded by a polynucleotide according to any one of (a) to (c), (a) a polynucleotide encoding a protein comprising an amino acid sequence in which one or more amino acid(s) in the amino acid sequence of SEQ ID NO: 17, 21, or 25 has been substituted, deleted, inserted, and/or added, (b) a polynucleotide which hybridizes with a polynucleotide comprising a nucleotide sequence of SEQ ID NO: 16, 20, or 24 under stringent conditions, (c) a polynucleotide encoding an amino acid sequence comprising 70% or more homology to the amino acid sequence of SEQ ID NO: 17, 21, or 25;

[12] a method for producing the enzyme of [1], which comprises the step of culturing a microorganism which belongs to genus *Torulaspora* and produces the enzyme of [1];

[13] the method of [12], wherein the microorganism belonging to the genus *Torulaspora* is *Torulaspora delbrueckii*;

[14] a method for producing the carbonyl reducing agent of [9], which comprises the step of culturing a transformant which has been transformed with a recombinant vector that comprises a polynucleotide according to any one of (a) to (e) as follows, (a) a polynucleotide comprising the nucleotide sequence of SEQ ID NO: 16, 20, or 24, (b) a polynucleotide encoding a protein comprising the amino acid sequence of SEQ ID NO: 17, 21, or 25, (c) a polynucleotide encoding a protein comprising an amino acid in which one or more amino acid(s) is substituted, deleted, inserted, and/or added to the amino acid sequence of SEQ ID NO: 17, 21, or 25, (d) a polynucleotide which hybridizes with a polynucleotide comprising the nucleotide sequence of SEQ ID NO: 16, 20, or 24 under stringent conditions, (e) a polynucleotide encoding an amino acid sequence comprising 70% or more homology to the amino acid sequence of SEQ ID NO: 17, 21, or 25;

[15] a method for producing an optically active alcohol, which comprises reacting a carbonyl reductase of any one of [1] to [4], the protein of [7], a microorganism producing the enzyme or the protein, the treated microorganism, the transformant of [10], or the carbonyl reducing agent of [11] with a ketone;

[16] a method for producing (S)-1-(3,4-dimethoxyphenyl)-2-propanol, which comprises reacting a carbonyl reductase of any one of [1] to [4], the protein of [7], a microorganism producing the enzyme or the protein, the treated microorganism, the transformant of [10], or the carbonyl reducing agent of [11] with 3,4-dimethoxyphenylacetone.

DETAILED DESCRIPTION OF THE INVENTION

Figure 1:
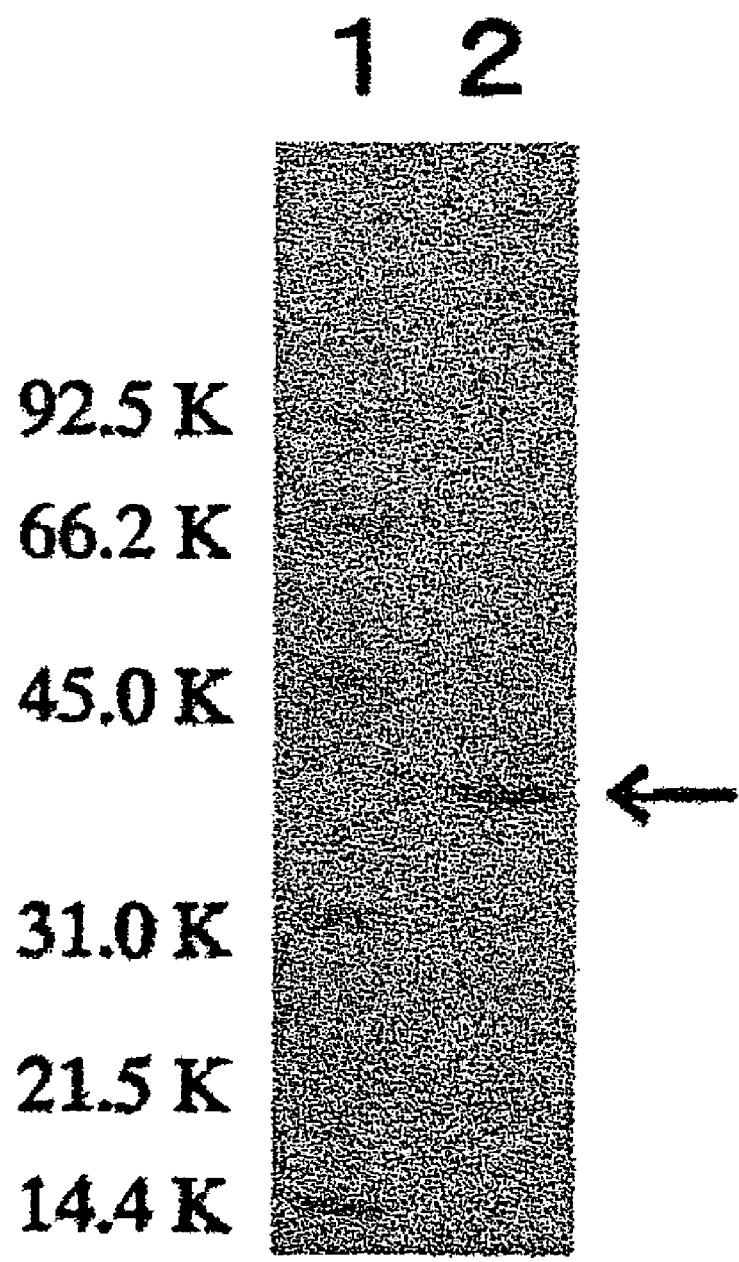
FIG. 1 shows an SDS-PAGE pattern. Lane 1 indicates a molecular weight marker and lane 2 indicates the enzyme obtained in Example 1.

The carbonyl reductases of the present invention can utilize NADPH as a coenzyme, have no alcohol dehydrogenating activity, and reduce 3,4-dimethoxyphenylacetone by utilizing NADPH as a coenzyme to produce 90% ee or more (S)-1-(3,4-dimethoxyphenyl)-2-propanol.

In the present invention, the activity of reducing 3,4-dimethoxyphenylacetone can be confirmed, for example, as follows:

A Method of Measuring the Activity of Reducing 3,4-dimethoxyphenylacetone:

A reaction solution comprising 50 mM potassium phosphate buffer (pH 6.5), 0.2 mM NADPH, 5 mM 3,4-dimethoxyphenylacetone, and an enzyme is reacted at 30° C. Any decrease in absorbance at 340 nm accompanying a decrease in NADPH is measured. 1U is defined as the amount of enzyme which catalyzes a 1 µmol decrease of NADPH in one minute.

A carbonyl reductase comprising the aforementioned physiochemical properties can be purified, for example, from a culture of yeast of the genus *Torulaspora*. In particular, *Torulaspora delbrueckii* is excellent for producing a carbonyl reductase of the present invention. Examples of *Torulaspora delbrueckii* which can be utilized for obtaining a carbonyl reductase of the present invention include IFO 0381 and JCM 5921.

*Torulaspora delbrueckii* can be cultured in a medium generally used for yeast culture, such as the YM medium. The microorganism is sufficiently grown, and the cells are collected. To obtain a cell-free extract, these cells are then disrupted in a buffer comprising a protease inhibitor and a reducing agent such as 2-mercaptoethanol and phenylmethanesulfonyl fluoride. The enzyme can be purified from the cell-free extract by appropriately combining fractionation utilizing the solubility of the protein (precipitation with an organic solvent and salt in gout with ammonium sulfate); cation exchange, an ion exchange, gel filtration, or hydrophobic chromatography; or affinity chromatography using a chelate, pigment, or antibody, etc. For example, the enzyme can be purified to an electrophoretically single band by hydrophobic chromatography using Phenyl-Sepharose™, anion exchange chromatography using MonoQ, hydrophobic chromatography using Butyl-Sepharose™, adsorption chromatography using hydroxyapatite, etc.

The *Torulaspora delbrueckii*-derived carbonyl reductases of the present invention are proteins comprising the following physiochemical properties of (1) and (2):

(1) action reduces ketones to produce an optically active alcohol by utilizing NADPH as a coenzyme;

(2) substrate specificity (a) utilizes NADPH as a coenzyme in the reduction reaction, (b) reduces 3,4-dimethoxyphenylacetone to produce (s)-1-(3,4-dimethoxyphenyl)-2-propanol, (c) comprises the activity of reducing 3,4-dimethoxyphenylacetone, but lacks the activity of oxidizing (S)-1-(3,4-dimethoxyphenyl)-2-propanol.

In addition, the carbonyl reductases of the present invention preferably comprise the physicochemical properties of (3) and (4):

(3) optimal pH pH 5.5 to 6.5, (4) molecular weight a molecular weight, determined via SDS-PAGE and gel filtration, of about 38,000.

The present invention relates to polynucleotides that encode carbonyl reductases, and their homologs. In this invention, the term "polynucleotide" refers to a polynucleotide removed from its original environment (e.g., the natural environment if naturally occurring) and thus, altered by the "hand of man" from its natural state. The term therefore covers, for example, (a) a DNA fragment of a naturally occurring genomic DNA molecule free of the coding sequences that naturally flank the nucleic acid (i.e., sequences located at the 5' and 3' ends of the nucleic acid) in the genomic DNA in the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library. There is no restriction on the length of the polynucleotide of the present invention, though it preferably comprises at least about 15 nucleotides, more preferably at least about 20, 30, 40, or 50 nucleotides, even more preferably at least about 100, 150, 200, 300, 400, 500, 1000, or 1500 nucleotides. The polynucleotides encoding the carbonyl reductases of the present invention comprise the nucleotide sequence of SEQ ID NO: 1. The nucleotide sequence of SEQ ID NO: 1 encodes a polypeptide comprising the amino acid sequence of SEQ ID NO: 2. The protein comprising this amino acid sequence constitutes preferred embodiments of the carbonyl reductases of the present invention.

A homologue of a polynucleotide encoding a carbonyl reductase of the present invention comprises a polynucleotide encoding a protein comprising the above-mentioned physicochemical properties (1) and (2), and comprising the amino acid sequence of SEQ ID NO: 2 in which one or more amino acids are deleted, substituted, inserted, and/or added. Amino acid substitutions may be made at one or more predicted, preferably nonessential amino acid residues. A "nonessential" amino acid residue is a residue that can be altered from the wild-type sequence of a protein without altering the biological activity, whereas an "essential" amino acid residue is required for biological activity. An amino acid is preferably substituted for a different amino acid(s) that allows the properties of the amino acid side-chain to be conserved. Accordingly, a "conservative amino acid substitution" is a replacement in which the amino acid residue is replaced with an amino acid residue having a chemically similar side chain. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). One skilled in the art can obtain the homolog of the polynucleotide by introducing a substitution, deletion, insertion, and/or addition mutation into the polynucleotide of SEQ ID NO: 1 using standard methods such as site-directed mutagenesis (Nucleic Acid Res. 10, pp. 6487 (1982); Methods in Enzymol. 100, pp. 448 (1983); Molecular Cloning 2nd Ed., Cold Spring Harbor Laboratory Press (1989); and PCR: A Practical Approach, IRL Press pp. 200 (1991)).

In addition, homologs of the polynucleotide of the present invention include polynucleotides hybridizing under stringent conditions to a polynucleotide comprising the nucleotide sequence of SEQ ID NO: 1, and encoding a protein comprising the above-mentioned physicochemical properties (1) and (2). Hybridization may be performed with buffers that permit the formation of a hybridization complex between nucleic acid sequences that contain some mismatches. The phrase "polynucleotide hybridizing under stringent conditions" means a polynucleotide hybridizing to a probe DNA that comprises one or more segments of at least 20 consecutive nucleotides, preferably at least 30 consecutive nucleotides, for example, 40, 60, or 100 consecutive nucleotides, arbitrarily selected from the nucleotide sequence of SEQ ID NO: 1 using methods such as ECL Direct Nucleic Acid Labeling and Detection System (Amersham Biosciences) under conditions recommended in the attached manual (for example, washing with the primary wash buffer comprising 0.5×SSC at 42° C.). Many factors determine the stringency of hybridization, including G+C content of the cDNA, salt concentration, and temperature. For example, stringency may be increased by reducing the concentration of salt or by raising the hybridization temperature. Temperature conditions for hybridization and washing greatly influence stringency and can be adjusted using melting temperature (Tm). Tm varies with the ratio of constitutive nucleotides in the hybridizing base pairs, and with the composition of the hybridization solution (concentrations of salts, formamide and sodium dodecyl sulfate). In solutions used for some membrane-based hybridization, addition of an organic solvent, such as formamide, allows the reaction to occur at a lower temperature. Accordingly, on considering the relevant parameters, one skilled in the art can select appropriate conditions to achieve a suitable stringency based experience or experimentation. More specifically, the expression "stringent conditions" generally refers to 42° C., 2×SSC, and 0.1% SDS; preferably 50° C., 2×SSC, and 0.1% SDS; and more preferably to 65° C., 0.1×SSC, and 0.1% SDS (highly stringent conditions), but is not particularly limited thereto. Polynucleotides isolated under stringent condition as described above are expected to encode polypeptides with higher homology at the amino acid level to the amino acid sequence shown in SEQ ID NO: 2.

Furthermore, the homologs of the polynucleotides of the present invention include a polynucleotide encoding a protein comprising at least 70% homology, preferably at least 80% homology, more preferably 90% or more, and most preferably 95% or more homology to the amino acid sequence of SEQ ID NO: 2. Protein homology searches can be performed, for example, on the Internet, in databases for protein amino acid sequences, such as SWISS-PROT, PIR, and DAD; DNA sequence databases, such as DDBJ, EMBL, and GenBank; databases for deduced amino acid sequences based on DNA sequences; by using the FASTA program, BLAST program, etc.

For the amino acid sequence of SEQ ID NO: 2, a homology search was performed on DAD using the BLAST program. As a result, among the known proteins, YOL151w (61%) produced by *Saccharomyces cerevisiae*, and ketoreductase (45%) produced by *Zygosaccharomyces rouxii* showed high homology. The expression "or more homology" in the present invention represents a value calculated using, for example, a program of the Lipman-Pearson method (Science, 227, 1435–1441 (1985)).

Specifically, a preferred embodiment of the present invention provides a polynucleotide according to any one of (c) to (e), as shown below, that encodes a protein comprising the physiochemical properties (1) and (2), shown above, as well as a protein encoded by the polynucleotide of the present invention.

(c) A polynucleotide encoding a protein comprising an amino acid sequence in which one or more amino acid(s) is substituted, deleted, inserted, and/or added to the amino acid sequence of SEQ ID NO: 2.

(d) A polynucleotide which hybridizes with a DNA comprising the nucleotide sequence of SEQ ID NO: 1 under stringent conditions.

(e) A polynucleotide encoding an amino acid sequence comprising 70% or more homology to the amino acid sequence of SEQ ID NO: 2.

In addition, the BLAST search found predicted open reading frames (ORFs) homologous to the carbonyl reductase of the present invention. However, the functions of these ORFs are unknown. Specifically, genome analysis of *Saccharomyces cerevisiae* resulted in three kinds of predicted ORF, designated as YGL157w, YGL039w, and YDR541c respectively. These predicted amino acid sequences have 57% 56%, and 61% homology to the carbonyl reductases of the present invention. In order to determine whether these predicted proteins comprise the carbonyl reductase activity of the present invention, primers were synthesized based on DNA sequences registered in DDBJ, and predicted ORFs were cloned from the genomic DNA of *Saccharomyces cerevisiae* using PCR. Each ORF was introduced into an expression vector, *Escherichia coli* (*E. coli*) was transformed to obtain a transformant, and cells were cultured to express each protein. As expected, YGL157w, YGL039w, and YDR541c showed the carbonyl reducing activity. In addition, these homologs reduced 3,4-dimethoxyphenylacetone to produce (S)-1-(3,4-dimethoxyphenyl)-2-propanol with a high optical purity.

Specifically, proteins comprising the amino acid sequence of SEQ ID NO: 17, 21, or 25 represent preferred embodiments of homologs of the carbonyl reductases of the present invention. The ORFs of these proteins were known, but their functions were unknown. The present inventors were the first to suggest that these proteins are carbonyl reductases. These proteins are extremely useful, and can be utilized as carbonyl-reducing agents for producing, for example, optically active alcohols (e.g. (S)-1-(3,4-dimethoxyphenyl)-2-propanol). The present inventors were first to discover the utility of the above proteins as carbonyl-reducing agents.

Therefore, a preferred embodiment of the present invention is a carbonyl-reducing agent, which comprises a protein comprising the physicochemical properties shown in (1) and (2) above, and which is encoded by a polynucleotide of any one of (a) to (e):

(a) a polynucleotide comprising the nucleotide sequence of SEQ ID NO: 16, 20, or 24, (b) a polynucleotide encoding a protein comprising the amino acid sequence of SEQ ID NO: 17, 21, or 25, (c) a polynucleotide encoding a protein comprising an amino acid sequence in which one or more amino acid(s) is substituted, deleted, inserted, and/or added to the amino acid sequence of SEQ ID NO: 17, 21, or 25, (d) a polynucleotide which hybridizes with a polynucleotide comprising the nucleotide sequence of SEQ ID NO: 16, 20, or 24 under stringent conditions, (e) a polynucleotide encoding an amino acid sequence comprising 70% or more homology to the amino acid sequence of SEQ ID NO: 17, 21, or 25.

A further preferred embodiment of the present invention provides a carbonyl-reducing agent, which comprises a protein comprising the physiochemical properties shown in (1) and (2) above, and the function of producing at least 80% ee or more (S)-1-(3,4-dimethoxyphenyl)-2-propanol, wherein the protein is encoded by a polynucleotide of any one of (a) to (c):

(a) a polynucleotide encoding a protein comprising an amino acid sequence in which one or more amino acid(s) is substituted, deleted, inserted, and/or added to the amino acid sequence of SEQ ID NO: 17, 21, or 25, (b) a polynucleotide which hybridizes with a polynucleotide comprising the nucleotide sequence of SEQ ID NO: 16, 20, or 24 under stringent conditions, (c) a polynucleotide encoding an amino acid sequence comprising 70% or more homology to the amino acid sequence of SEQ ID NO: 17, 21, or 25.

The present invention relates to a protein comprising the amino acid sequence of SEQ ID NO: 2. The present invention also comprises a homolog of a protein comprising the amino acid sequence of SEQ ID NO: 2.

"A homolog of the carbonyl reductase" of the present invention means a protein comprising an amino acid sequence in which one or more amino acid(s) is substituted, deleted, inserted, and/or added to the amino acid sequence of SEQ ID NO: 2, where the protein is functionally equivalent to a protein comprising the amino acid sequence of SEQ ID NO: 2. In the present invention, "functionally equivalent to a protein comprising the amino acid sequence of SEQ ID NO: 2" means that the protein has the physiochemical properties shown in the aforementioned (1) to (2). A person skilled in the art can obtain a polynucleotide encoding a homolog of a carbonyl reductase by appropriately introducing a substitution, deletion, insertion, and/or addition mutation in to the DNA of SEQ ID NO: 1 using site-directed mutagenesis (Nucleic Acid Res. 10, pp. 6487 (1982), Methods in Enzymol. 100, pp. 448 (1983), Molecular Cloning $2^{nd}$ Ed., Cold Spring Harbor Laboratory Press (1989), PCR: A practical Approach IRL Press pp. 200 (1991)). By introducing a polynucleotide which encodes a carbonyl reductase homolog into a host, and then expressing it, a homolog of a carbonyl reductase of SEQ ID NO: 2 can be obtained.

The number of amino acids that may be substituted, deleted, inserted, and/or added is not particularly restricted, so long as the protein remains functionally equivalent to a protein comprising the amino acid sequence of SEQ ID NO: 2. Generally, up to about 50 amino acids may be changed, preferably up to about 30 amino acids, more preferably up to about 10 amino acids, and even more preferably up to about 3 amino acids. Likewise, the site of mutation is not particularly restricted, so long as the mutation does not result in the disruption of the function of the protein.

The carbonyl reductase homologs of the present invention include a protein which comprises at least 70% identity, preferably at least 80% identity, and more preferably 90% or more identity, even more preferably 95% or more homology to the amino acid sequence of SEQ ID NO: 2. Protein homology searches can be performed, for example, on the Internet, using databases for protein amino acid sequences such as SWISS-PROT, PIR, and DAD; DNA sequence databases such as DDBJ, EMBL, or GenBank; or databases for deduced amino acid sequences based on DNA sequences; by using the FASTA program, BLAST program, etc.

A polynucleotide encoding the carbonyl reductase of the present invention may be isolated, for example, using the following procedure:

The DNA of the present invention can be obtained using PCR by designing PCR primers based on the nucleotide sequence of SEQ ID NO: 1, and using chromosomal DNA or a cDNA library of an enzyme-producing strain as a template.

Furthermore, by using the obtained DNA fragment as a probe, a polynucleotide of the present invention can be obtained by colony or plaque hybridization using a cDNA library, or a library obtained by transforming *E. coli* with a phage or plasmid into which restriction enzyme digestion products of the chromosomal DNA of the enzyme-producing strain has been introduced.

A polynucleotide of the present invention can also be obtained by analyzing the nucleotide sequence of the DNA fragment obtained by PCR, using this sequence to design PCR primers that will extend the known DNA outward, digesting the enzyme-producing strain's chromosomal DNA with appropriate restriction enzyme(s), and then using self-ligated circular DNA as a template to perform reverse PCR (Genetics 120, 621–623 (1988)). Alternatively, the Rapid Amplification of cDNA Ends (RACE) method ("Experimental manual for PCR" pp. 25–33, HBJ Press) can be used.

A polynucleotide of the present invention comprises not only genomic DNA and cDNA cloned using the above-mentioned methods, but also chemically synthesized DNA.

By inserting a thus-isolated polynucleotide encoding a carbonyl reductase of the present invention into a known expression vector, a carbonyl reductase expression vector can be provided. That is, the present invention relates to a recombinant vector comprising a polynucleotide of the present invention. A preferred embodiment of the present invention provides a vector comprising a polynucleotide of the present invention. Examples of the vector of the present invention include pSE-TDR1, pSE-YDR1, pSE-YGP7, and pSE-YGD9, in which a gene encoding a carbonyl reductase is introduced in an expressible state in to E. coli expression vector pSE420D. In addition, the recombinant vector of the present invention can comprise a coenzyme-regenerating dehydrogenase gene, described below.

Furthermore, by culturing a transformant that has been transformed with this expression vector, a carbonyl reductase of the present invention can be obtained from the transformant.

A specific microorganism transformed to express a carbonyl reductase of the present invention may be any organism, as long as it is transformed with a recombinant vector comprising a polynucleotide encoding a polypeptide comprising a carbonyl reductase, and it can express carbonyl reductase activity. The present invention provides transformants transformed with a polynucleotide of the present invention, or a vector of the present invention.

Non-limiting examples of microorganisms that can be transformed in the present invention are those for which host-vector systems are available, and include the following:

Bacteria such as:
  the genus *Escherichia*
  the genus *Bacillus*
  the genus *Pseudomonas*
  the genus *Serratia*
  the genus *Brevibacterium*
  the genus *Corynebacterium*
  the genus *Streptococcus*
  the genus *Lactobacillus;*

Actinomycetes such as:
  the genus *Rhodococcus*
  the genus *Streptomyces;*

Yeasts such as
  the genus *Saccharomyces*
  the genus *Kluyveromyces*
  the genus *Schizosaccharomyces*
  the genus *Zygosaccharomyces*
  the genus *Yarrowia*
  the genus Trichosporon
  the genus Rhodosporidium
  the genus *Pichia*
  the genus *Candida*; and Fungi such as
  the genus *Neurospora*
  the genus *Aspergillus*
  the genus *Cephalosporium*
  the genus *Trichoderma.*

Procedures for preparing a transformant and constructing a recombinant vector suitable for a host can be carried out by employing techniques commonly used in the fields of molecular biology, bioengineering, and genetic engineering (for example, see Sambrook et al., "Molecular Cloning", Cold Spring Harbor Laboratories (2001)). To express in a microorganism a gene that encodes a carbonyl reductase of the present invention, which utilizes NADPH as an electron donor, it is necessary to introduce the DNA into a plasmid vector or phaqe vector that is stable in that microorganism, and to transcribe and translate the genetic information.

To achieve this, a promoter, a unit for regulating transcription and translation, is placed upstream of the 5' end of the DNA of the present invention, and preferably, a terminator is placed downstream of the 3' end of the DNA. The promoter and terminator should be functional in the microorganism to be used as host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75–102 (1990)" and "Yeast 8, 423–488 (1992)".

For example, for the genus *Escherichia*, and in particular for *Escherichia coli*, available plasmids include the pBR series and pUC series plasmids; available promoters include promoters derived from lac (derived from β-galactosidase gene), trp (derived from the tryptophan operon), tac and trc (which are chimeras of lac and trp), and PL and PR of λ phage. Available terminators are derived from trpA, phages, rrnB ribosomal RNA, etc. Of these, vector pSE420D (described in JP-A 2000-189170), which is produced by modifying a part of multicloning site of commercially available pSE420 (Invitrogen), can be suitably utilized.

For the genus *Bacillus*, available vectors are pUB110 series and pC194 series plasmids, and can be integrated into a host chromosome. Available promoters and terminators are derived from apr (alkaline protease), npr (neutral protease), amy (α-amylase), etc.

For the genus *Pseudomonas*, there are host-vector systems developed for *Pseudomonas putida* and *Pseudomonas cepacia*. A broad-host-range vector, pKT240, (comprising RSF1010-derived genes required for autonomous replication) based on TOL plasmid, which is involved in decomposition of toluene compounds, is available. A promoter and a terminator derived from the lipase gene (JP-A Hei 5-284973) are also available.

For the genus *Brevibacterium*, and in particular for *Brevibacterium lactofermentum*, available plasmid vectors include pAJ43 (Gene 39, 281–286 (1985)). Promoters and terminators used for *Escherichia coli* can be utilized for *Brevibacterium* without any modification.

For the genus *Corynebacterium*, and in particular for *Corynebacterium glutamicum*, plasmid vectors such as pCS11 (JP-A Sho 57-183799) and pCB101 (Mol. Gen. Genet. 196, 175 (1984)) are available.

For the genus *Streptococcus*, plasmid vectors such as pHV1301 (FEMS Microbiol. Lett. 26, 239 (1985)) and pGKl (Appl. Environ. Microbiol. 50, 94 (1985)) can be used.

For the genus *Lactobacillus*, plasmid vectors such as pAMβ1 (J. Bacteriol. 137, 614 (1979)), which was developed for the genus *Streptococcus*, can be utilized. Promoters that are used for *Escherichia coli* can also be used.

For the genus *Rhodococcus*, plasmid vectors isolated from *Rhodococcus rhodochrous* are available (J. Gen. Microbiol. 138, 1003 (1992)).

For the genus *Streptomyces*, plasmids can be constructed in accordance with the method described in "Genetic Manipulation of Streptomyces: A Laboratory Manual"[1] (Hopwood et al, Cold Spring Harbor Laboratories (1985)). In particular, for *Streptomyces lividans*, pIJ486 (Mol. Gen. Genet. 203, 468–478, 1986), pKC1064 (Gene 103, 97–99 (1991)), and pUWL-KS (Gene 165, 149–150 (1995)) can be used. The same plasmids can also be utilized for *Streptomyces virginiae* (Actinomycetol. 11, 46–53 (1997)).

For the genus *Saccharomyces*, and in particular for *Saccharomyces cerevisiae*, YRp series, YEp series, YCp series, and YIp series plasmids are available. In addition, integration vectors (see EP 537456, and such), which are integrated into a chromosome via homologous recombination with multicopy-ribosomal genes, allow the introduction of a gene of interest in multicopy, and the gene incorporated can be stably maintained in the microorganism. Thus, this type of vector is highly useful. Available promoters and terminators are derived from genes encoding alcohol dehydrogenase (ADH), glyceraldehyde-3-phosphate dehydrogenase (GAPDH), acid phosphatase (PHO), β-galactosidase (GAL), phosphoglycerate kinase (PGK), enolase (ENO), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol. 145, 382–390 (1981)), plasmids derived from pGKl1 and involved in killer activity, KARS (*Kluyveromyces* autonomous replication sequence) series plasmids, and plasmids capable of being integrated into a chromosome via homologous recombination with ribosomal DNA (see, EP 537456, etc.). Promoters and terminators derived from ADH, PGK, and so on are also available.

For the genus *Schizosaccharomyces*, it is possible to use plasmid vectors comprising autonomous replication sequence (ARS) derived from *Schizosaccharomyces pombe* and auxotrophy-complementing selectable markers derived from *Saccharomyces cerevisiae* (Mol. Cell. Biol. 6, 80 (1986)). Promoters such as ADH promoter derived from *Schizosaccharomyces pombe* can also be used (EMBO J. 6, 729 (1987)). In particular, pAUR224 is commercially available from TaKaRa Shuzo Co., Ltd.

For the genus *Zygosaccharomyces*, plasmid vectors originating from those such as pSB3 (Nucleic Acids Res. 13, 4267 (1985)) derived from *Zygosaccharomyces rouxii* are available. In addition, it is possible to use promoters such as PHO5 promoter derived from *Saccharomyces cerevisiae* and GAP-Zr (Glyceraldehyde-3-phosphate dehydrogenase) promoter (Agri. Biol. Chem. 54, 2521 (1990)) derived from *Zygosaccharomyces rouxii*.

For the genus *Pichia*, a host vector system has been developed for *Pichia angusta* (previously called *Hansenula polymorpha*). Although *Pichia angusta*-derived autonomous replication sequences (HARS1 and HARS2) are available as vectors, they are rather unstable, and thus multicopy chromosomal integration is effective (Yeast 7, 431–443 (1991)). In addition, methanol-induced promoters of alcohol oxidase (AOX) and format dehydrogenase (FDH) and the like are available. Furthermore, host-vector systems originating from *Pichia*-derived autonomous replication sequences (PARS1, PARS2) have been developed (Mol. Cell. Biol. 5, 3376 (1985)). A highly efficient promoter, such as AOX promoter, which is inducible by high-cell-density-culture and methanol can also be employed (Nucleic Acids Res. 15, 3859 (1987)).

In the genus *Candida*, host-vector systems have been developed for *Candida maltosa*, *Candida albicans*, *Candida tropicalis*, *Candida utilis*, etc. An ARS originating from *Candida maltosa* has been cloned (Agri. Biol. Chem. 51,51, 1587 (1987)), and a vector using this sequence has been developed for *Candida maltosa*. Furthermore, a chromosome-integration vector with a highly efficient promoter has been developed for *Candida utilis* (JP-A Hei 08–173170).

Of fungi, *Aspergillus niger* and *Aspergillus oryzae* of the genus *Aspergillus* have been extensively studied, and thus plasmid vectors and chromosome-integration vectors are available, as well as promoters derived from an extracellular protease gene and amylase gene (Trends in Biotechnology 7, 283–287 (1989)).

In the genus *Trichoderma*, host-vector systems have been developed for *Trichoderma reesei*, and promoters such as those derived from extracellular cellulase genes are available (Biotechnology 7, 596–603 (1989)).

Various host-vector systems have also been developed for plants and animals. In particular, systems include those of insects such as silkworm (Nature 315, 592–594 (1985)), and plants such as rapeseed, maize, and potato. These systems are preferably used to express a large amount of foreign protein.

The microorganisms with the ability to produce carbonyl reductase used in this invention comprise all strains, mutants, and variants with the ability to produce carbonyl reductase, as well as transformants constructed by genetic engineering and with the ability to produce the enzyme of the present invention.

The present invention relates to methods for producing an optically active alcohol, in particular, for producing (S)-1-(3,4-dimethoxyphenyl)-2-propanol by reducing ketones utilizing an aforementioned carbonyl reductase, and to uses of this alcohol. A preferred embodiment of the present invention provides a method for producing an enzyme of the present invention, where the method comprises the step of culturing a microorganism of the genus *Torulaspora* which produces a carbonyl reductase of the present invention. Furthermore, the present invention provides a method for producing a carbonyl reductase of the present invention, which comprises the step of culturing the aforementioned transformant of the present invention. An optically active alcohol can be produced using the desired enzyme reaction, performed by contacting a reaction solution with an enzyme molecule, a treated enzyme molecule, a culture comprising an enzyme molecule, or a transformant such as a microorganism that produces an enzyme. The specific mode by which an enzyme is contacted with a reaction solution is not limited to these particular examples. Examples of a microorganism used in the aforementioned methods preferably include *Torulaspora delbrueckii*.

A preferred embodiment of a method for producing an optically active alcohol of the present invention provides a method for producing an optically active alcohol, which comprises reacting a ketone with a carbonyl reductase of the present invention, a protein of the present invention, a microorganism which produces the enzyme or the protein, the treated microorganism, a transformant of the present invention, or a carbonyl reducing agent of the present invention. In addition, one example of the methods of the present invention is a method for producing (S)-1-(3,4-dimethoxyphenyl)-2-propanol, which comprises reacting 3,4-dimethoxyphenylacetone with a carbonyl reductase of the present invention, a protein of the present invention, a microorganism which produces the enzyme or the protein, the treated microorganism, a transformant of the present invention, or a carbonyl reducing agent of the present invention.

More specifically, examples of the treated microorganism comprising carbonyl reductase in the present invention comprise a microorganism in which the permeability of a cell membrane has been changed by treatment with a surfactant or an organic solvent such as toluene, a cell-free extract obtained by disrupting cells by treatment with glass beads or an enzyme, and a partially purified extract.

As a ketone in a method for producing an optically active alcohol of the present invention, 1-acetoxy-2-propanone, ethyl acetoacetate, methyl acetoacetate, ethyl 4-chloroacetoacetate, methyl 4-chloroacetoacetate, 2-chloro-1-(3'-chlorophenyl)ethanone, or 3,4-dimethoxyphenylacetone can be preferably used, and (S)-1-acetoxy-2-propanol, ethyl (S)-3-hydroxybutanoate, methyl (S)-3-hydroxybutanoate, ethyl (R)-4-chloro-3-hydroxybutanoate, methyl (R)-4-chloro-3-hydroxybutanoate, (R)-2-chloro-1-(3'-chlorophenyl)ethanol, and (S)-1-(3,4-dimetoxyphenyl)-2-propanol can be produced.

A preferred embodiment of the present invention provides a method for producing (S)-1-(3,4-dimethoxyphenyl)-2-propanol, which comprises reacting 3,4-dimethoxyphenylacetone with a carbonyl reductase of the present invention, a protein comprising the carbonyl-reducing activity, a microorganism which produces the enzyme or the protein, or the treated microorganism.

NADPH regeneration using the NADP+ produced from NADPH in the aforementioned reduction reaction can be performed using the NADP$^+$-reducing ability of microorganisms (glycolysis system, C1 assimilation pathway of methylotrophs, etc.). NADP$^+$-reducing ability can be enhanced by adding glucose or ethanol to a reaction system. Alternatively, reducing ability can also be enhanced by adding to the reaction system a microorganism with the ability to produce NADPH from NADP+, or that treated microorganism, or an enzyme. For example, NADPH regeneration can be performed by using a microorganism comprising glucose dehydrogenase, alcohol dehydrogenase, formate dehydrogenase, amino acid dehyrogenase, or organic acid dehydrogenase (such as malate dehydrogenase), the treated microorganism, or a partially purified or purified enzyme. These components, which constitute a necessary reaction for regenerating NADPH, can be contacted by addition to a reaction system for producing an optically active alcohol of the present invention, by adding immobilized components thereto, or by using a membrane that can exchange NADPH.

The present invention also relates to methods for producing a protein comprising the carbonyl-reducing activity of the present invention, which include the step of culturing a transformant transformed with a recombinant vector comprising a polynucleotide of the present invention. In some cases in the present methods, when a live cell of a microorganism, transformed with a recombinant vector comprising a polynucleotide of the present invention, is utilized in a method for producing the aforementioned optically active alcohol, an additional reaction system for regenerating NADPH may be unnecessary. Specifically, by using a microorganism with a high NADPH regenerating activity, the reduction reaction using a transformant can be efficiently performed without the addition of an NADPH-regenerating enzyme. Furthermore, the host can be introduced both with a DNA encoding an NADPH-dependent carbonyl reductase of the present invention, and a gene useful in regenerating NADPH (a coenzyme regenerating dehydrogenase gene), for example that of a glucose dehydrogenase, alcohol dehydrogenase, formate dehydrogenase, amino acid dehydrogenase, or organic acid dehydrogenase (such as malate dehydrogenase). This will result in more efficient expression of the NADPH-regenerating enzyme and the NADPH-dependent carbonyl reductase, and a more efficient reduction reaction. When introducing two or more of these genes into a host, in order to avoid incompatibility, methods such as the following can be used: a method for transforming the host with multiple recombinant vectors into which genes have been separately introduced and where the vectors have different replication origins; a method in which the two or more genes are introduced into a single vector; or a method for introducing a number of or one of the genes into chromosomes.

When multiple genes are introduced into a single vector, each gene can be ligated to a region involved in the regulation of expression, such as a promotor or terminater. Multiple genes can also be expressed as an operon comprising multiple cistrons, such as the lactose operon.

As an NADPH-regenerating enzyme, for example, a glucose dehydrogenase derived from *Bacillus subtilis* or *Thermoplasma acidophilum* can be utilized. Specifically, preferably utilized recombinant vectors include pSG-TDR1, pSG-YDR1, pSG-YGP7, and pSG-YGD9 vectors into which a carbonyl reductase gene and a glucose dehydrogenase gene derived from *Bacillus subtilis* have been introduced.

A reduction reaction using an enzyme of the present invention can be performed in water, in a water-insoluble organic solvent such as ethyl acetate, butyl acetate, toluene, chloroform, n-hexane, methyl isobutyl ketone, and methyl tertiary butyl ester; in a two-phase system with an aqueous medium, or in a mixture system with a water-soluble organic solvent such as methanol, ethanol, isopropyl alcohol, acetonitrile, acetone, and dimethyl sulfoxide. The reaction in the present invention may be performed by utilizing an immobilized enzyme or a membrane reactor.

The reaction of the present invention can be performed at a temperature range of 40C to 60° C., preferably at 15° C. to 37° C.; at a pH of 3 to 11, preferably pH 5 to 9; and at a substrate concentration of 0.01% to 50%, preferably 0.1% to 20%, more preferably 0.1% to 10%. If necessary, coenzyme NADP$^+$ or NADPH may be added to the reaction system at 0.001 mM to 100 mM, more preferably at 0.01 mM to 10 mM. Although a substrate may be added at once at the beginning of the reaction, it is preferable to add it continuously or discontinuously, such that the substrate concentration in the reaction solution does not become too high.

When regenerating NADPH, for example, glucose (when using glucose dehydrogenase) or ethanol/isopropanol (when using alcohol dehydrogenase) is added to the reaction system. These compounds may be added at a molar ratio relative to a substrate ketone of 0.1- to 20-fold, preferably in excess at 1- to 5-fold. On the other hand, a NADPH-regenerating enzyme such as glucose dehydrogenase or alcohol dehydrogenase can be added at approximately 0.1- to 100-fold, and preferably at 0.5- to 20-fold of the enzyme activity compared with the NADPH-dependent carbonyl reductase of the present invention.

Purification of an optically active alcohol produced by reduction of a ketone in the present invention can be performed by appropriately combining the centrifugation of cells and proteins, separation by membrane treatment, solvent extraction, distillation, etc.

For example, (S)-1-(3,4-dimethoxyphenyl)-2-propanol can be obtained as an optically active alcohol by centrifuging a reaction solution comprising microorganism cells to remove the cells, extracting with ethyl acetate, butyl acetate, toluene, hexane, benzene, methyl isobutyl ketone, methyl tertiary butyl ether, or butanol, and then performing vacuum concentration. The purity of the reaction product can be further increased by using silica gel column chromatography, etc.

NADPH-dependent carbonyl reductases useful for producing an optically active alcohol has been provided. By utilizing the present enzymes, methods for efficiently producing high optical purity (S)-1-(3,4-dimethoxyphenyl)-2-propanol from 3,4-dimethoxyphenylacetone have been provided.

The words "a", "an", and "the" as used herein mean "at least one" unless otherwise specifically indicated. Furthermore, all patents, published patent applications, and publications cited herein are incorporated by reference in their entirety.

Herein, the present invention will be specifically described below using Examples. However, it is not to be construed as being limited thereto.

EXAMPLE 1

Purification of a Carbonyl Reductase

Cells for enzyme purification were prepared by culturing Torulaspora delprueckii JCM 5921 strain in 1.2 L of YM medium (glucose 20 g/L, yeast extract 3 g/l, malt extract 3 g/L, peptone 5 g/L, pH 6.0), followed by centrifugation. The resulting wet cells were suspended in a solution containing 50 mM Tris-HCl buffer (pH 8.5), 0.02% 2-mercaptoethanol, and 2 mM phenylmethanesulfonyl fluoride (PMSF), and homogenized with a bead beater (Biospec). The cell residue was then removed by centrifugation to obtain a cell-free extract. Protamine sulfate was added to the cell-free extract, which was then centrifuged to remove nucleic acids and obtain the supernatant. Ammonium sulfate was then added to the supernatant to 30% saturation, and this was added to Phenyl-Sepharose™ HP (2.6 cm×10 cm) equilibrated with a standard buffer (10 mM Tris-HCl buffer (pH 8.5), 0.01% 2-mercaptoethanol, and 10% glycerol) comprising 30% ammonium sulfate. The present enzyme was then eluted using ammonium sulfate over a concentration gradient of 30% to 0%. NADPH-dependent 3,4-dimethoxyphenylacetone-reducing activity was observed in the gradient eluted fractions, and the eluted peak part was collected and then concentrated by ultrafiltration.

The concentrated enzyme solution was dialyzed against a standard buffer, added to MonoQ (0.5 cm×5 cm) equilibrated with the same buffer, and subjected to elution with sodium chloride over a gradient concentration of 0 M to 0.5M. The eluted active fraction was collected, and subjected to ultrafiltration to obtain the concentrated enzyme solution.

The concentrated enzyme solution was dialyzed against 5 mM potassium phosphate buffer (pH 8.0) comprising 0.01%2-mercaptoethanol and 10% glycerol, added to a hydroxyapatite column (0.5 cm×10 cm) equilibrated with the same buffer, and then subjected to gradient elution with potassium phosphate buffer (pH 8.0) over 5 mM to 350 mM. The eluted active fraction comprising the highest specific activity was analyzed using SDS-PAGE. As a result, a single band consisting of only the present enzyme was obtained (FIG. 1).

The specific activity of the purified enzyme was 196 mU/mg. A summary of the purification is shown in Table 1.

TABLE 1

| Step | Protein (mg) | Enzyme activity (U) | Specific activity (mU/mg) |
|---|---|---|---|
| Cell-free extract | 15,000 | — | — |
| Nucleic acid removal | 6,580 | 24.1 | 3.66 |
| Butyl-Toyopearl | 377 | 7.00 | 18.6 |

TABLE 1-continued

| Step | Protein (mg) | Enzyme activity (U) | Specific activity (mU/mg) |
|---|---|---|---|
| MonoQ | 31.4 | 3.75 | 119 |
| Hydroxyapatite | 0.245 | 0.048 | 196 |

EXAMPLE 2

Measurement of Molecular Weight of the Carbonyl Reductase

The molecular weight of a subunit of the enzyme obtained in Example 1 was about 38,000, as determined using SDS-PAGE. The molecular weight was also measured separately using a Superdex G200 gel filtration column, and was again found to be about 38,000. Therefore, the present enzyme was presumed to be a monomer.

EXAMPLE 3

Optimal pH

Figure 2:
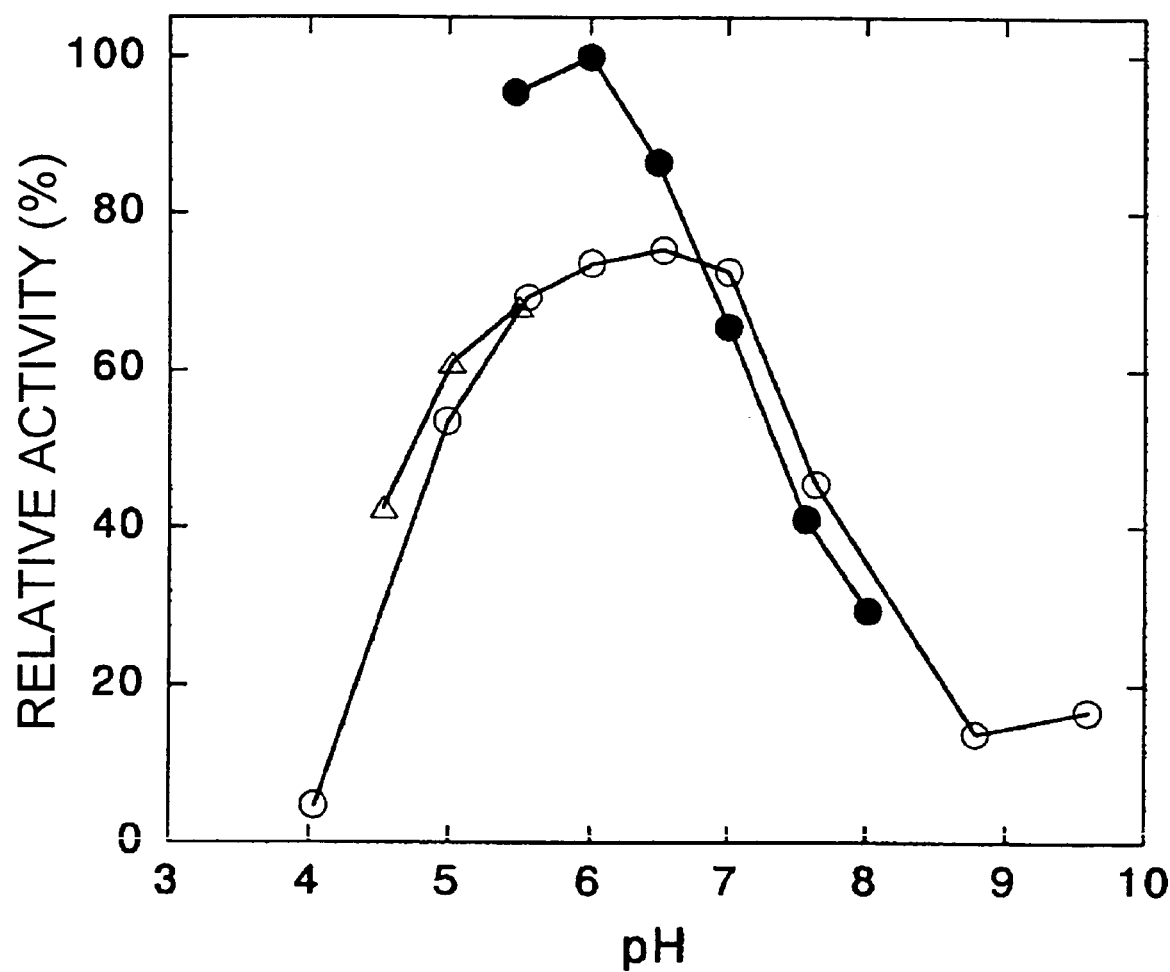
FIG. 2 is a graph showing the pH dependency of the 3,4-dimethoxyphenylacetone-reducing activity of the enzyme obtained in Example 1. An open circle represents a Britton and Robinson buffer, a triangle represents an acetic acid-sodium acetate buffer, and a filled circle represents a potassium phosphate buffer.

By changing the pH using potassium phosphate buffer, sodium acetate buffer, and Britton-Robinson buffer, the 3,4-dimethoxyphenylacetone-reducing activity of the enzyme obtained in Example 1 was investigated. Activity at each pH was expressed as a relative activity, where the maximum activity was regarded as 100 (FIG. 2). Optimal pH (showing 80% or more relative activity) was 5.5 to 6.5.

EXAMPLE 4

Optimal Temperature

Figure 3:
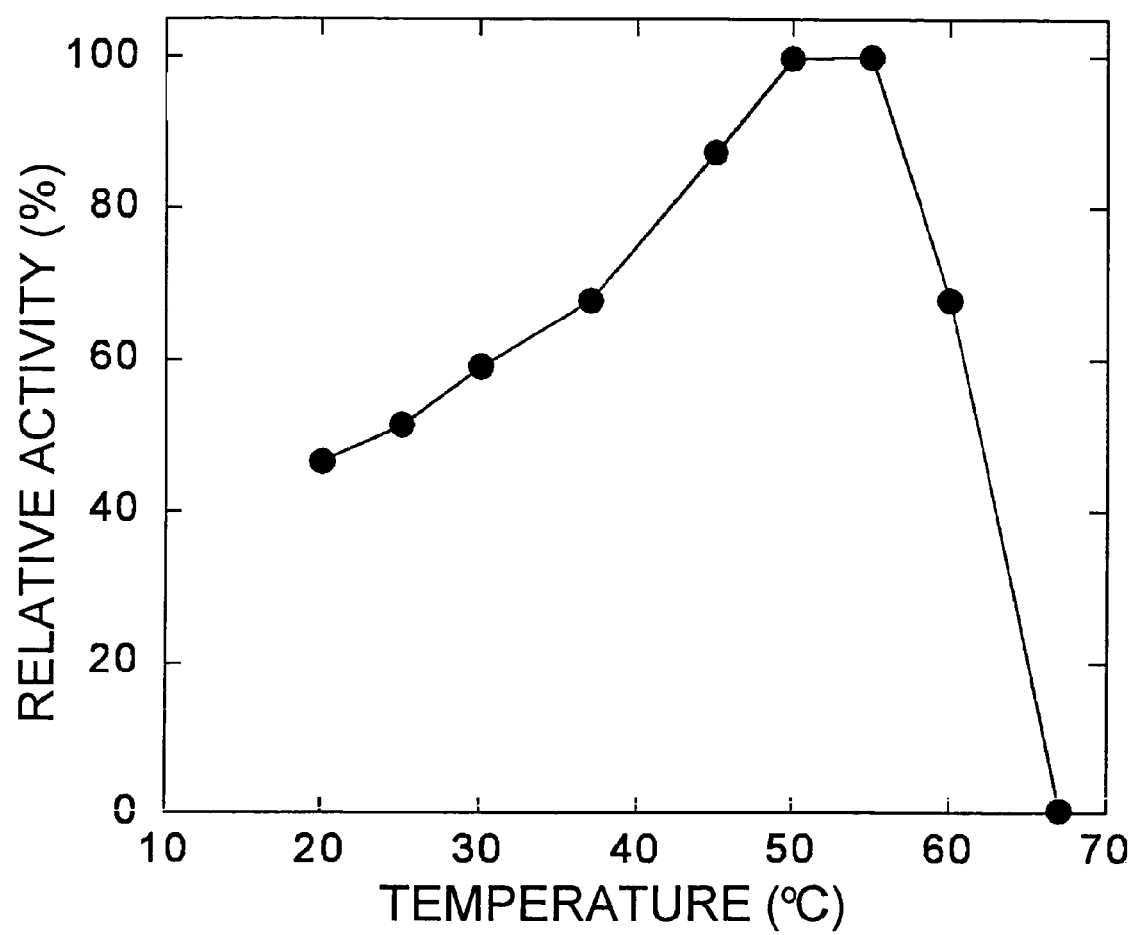
FIG. 3 is a graph showing temperature dependency of the 3,4-dimethoxyphenylacetone-reducing activity of the enzyme obtained in Example 1.

Of the standard reaction conditions, only the temperature was changed, and the 3,4-dimethoxyphenylacetone-reducing activity of the enzyme obtained in Example 1 was then measured. Activity at each temperature was expressed as a relative activity, where the maximum activity was regarded as 100 (FIG. 3). Optimal temperature (showing 80% or more relative activity) was 50° C. to 55° C.

EXAMPLE 5

Substrate Specificity

The enzyme obtained in Example 1 was reacted with various ketones, ketoesters, and soon. The activities of the reduction reactions were expressed as relative activities, where the reduction of 3,4-dimethoxyphenylacetone was regarded as 100 (Table 2) (substrate specificity of carbonyl reductase). The activity of dehydrogenating 1-(3,4-dimethoxyphenyl)-2-propanol was measured as follows: A reaction was performed at 30° C. in a reaction solution comprising 50 mM Tris-HCl buffer (pH 8.5), 2.5 mM NADP$^+$, 5 mM 1-(3,4-dimethoxyphenyl)-2-propanol, and the enzyme. An increase in absorbance at 340 nm, accompanying NADPH production, was measured. 1 U was defined as the amount of enzyme catalyzing the production of 1 μmol NADPH per minute. In addition, the activity of reducing NADH-dependent 3,4-dimethoxyphenylacetone was measured as follows: A reaction was performed at 30° C. in a reaction solution comprising 50 mM potassium phosphate buffer (pH 6.5), 0.2 mM NADH, 5 mM 3,4-dimethoxyphenylacetone, and the enzyme, and decrease in absorbance at 340 nm, accompanying decrease in NADH, was measured. 1 U was defined as the amount of enzyme catalyzing a decrease of 1 μmol NADH per minute.

TABLE 2

| Substrate | Concentration (mM) | Coenzyme | Relative activity (%) |
|---|---|---|---|
| 3,4-Dimethoxyphenylacetone | 5 | NADPH | 100 |
| 3,4-Dimethoxyphenylacetone | 5 | NADH | 0.0 |
| (S)-1-(3,4-dimethoxyphenyl)-2-propanol | 5 | NADP+ | 0.0 |
| (R)-1-(3,4-dimethoxyphenyl)-2-propanol | 5 | NADP+ | 0.0 |
| Ethyl acetoacetate | 20 | NADPH | 3170 |
| Methyl acetoacetate | 20 | NADPH | 3670 |
| Ethyl 4-chloroacetoacetate | 20 | NADPH | 6780 |
| Methyl 4-chloroacetoacetate | 20 | NADPH | 8040 |
| 2-Chloro-1-(3'-chlorophenyl)ethanone | 2 | NADPH | 922 |
| 2,3-Butanedione | 20 | NADPH | 1480 |
| 2,4-Pentanedione | 20 | NADPH | 422 |
| Acetophenone | 20 | NADPH | 256 |
| 1-Acetoxy-2-propanone | 20 | NADPH | 24700 |
| 2-Acetoxycyclopentanone | 20 | NADPH | 567 |
| 4'-Methoxypropiophenone | 20 | NADPH | 283 |
| Benzylacetone | 20 | NADPH | 739 |
| Phenoxy-2-propanone | 20 | NADPH | 939 |
| 2-Acetoxy-3-butanone | 20 | NADPH | 589 |
| Methyl pyruvate | 20 | NADPH | 1320 |
| Camphorquinone | 1 | NADPH | 644 |
| 2,3-Pentanedione | 20 | NADPH | 2590 |
| Methoxyacetone | 20 | NADPH | 117 |

EXAMPLE 6

Synthesis of (S)-1-(3,4-Dimethoxyphenyl)-2-propanol Using the Carbonyl Reductase A reaction was performed overnight at 25° C. in 1 mL of a reaction solution comprising 200 mM potassium phosphate buffer (pH 6.5), 1 mM NADP+, 2 U glucose dehydroganase (Wako Pure Chemical Industries, Ltd.), 250 mM glucose, 0.25 U carbonyl reductase, and 50 mM 3,4-dimethoxyphenylacetone. The optical purity of the produced (S)-1-(3,4-dimethoxyphenyl)-2-propanol was measured as follows: One mL of ethyl acetate was added to 0.5 mL of the reaction solution to extract (S)-1-(3,4-dimethoxyphenyl)-2-propanol, and the extraction solvent was desolvated. 0.5 mL of a dissolving solution (n-hexane: isopropanol=4:1) was then added to dissolve the extract, which was then analyzed by liquid chromatography using an optical resolution column. CHIRALCEL OF (4.6 mm×25 cm; Daicel Chemical Industries, Ltd.) was used as the optical resolution column. Chromatography was performed with a wavelength of 220 nm, a flow rate of 1.0 mL/min, and at 40° C. using an eluting solution of n-hexane: isopropanol=4:1. The (S)-1-(3,4-dimethoxyphenyl)-2-propanol produced by the present invention had a purity of 99% ee or more.

In addition, the (S)-1-(3,4-dimethoxyphenyl)-2-propanol thus-produced was quantified using gas chromatography, and a yield relative to the raw starting material, 3,4-dimethoxyphenylacetone, was obtained. Specifically, the analysis was performed at a column temperature of 210° C., using Thermon 3000 (10%)-Chromosorb W (AW-DMCS, Mesh 60–80; 3.2 mm×210 cm) with a hydrogen flame ionization detector (FID). The resulting reaction yield was about 95%.

EXAMPLE 7

Partial Amino Acid Sequence of the Carbonyl Reductase

The N-terminal amino acid sequence of the enzyme obtained in Example 1 was analyzed using a protein sequencer. The amino acid sequence is shown in SEQ ID NO: 3. In addition, a gel fragment comprising carbonyl reductase was excised from an SDS-PAGE gel, washed twice, and subjected to overnight in-gel digestion at 35° C., using a lysyl endopeptidase. The digested peptide was separated and collected by gradient elution of acetonitrile in 0.1% trifluoroacetic acid using reverse phase HPLC (TSK gel ODS-80-Ts, 2.0 mm×250 mm; Tosoh Corporation).

The obtained peptide peak was named lep_41, and its amino acid sequence was analyzed using a protein sequencer (Hewlett Packard G1005A Protein Sequence System). The amino acid sequence of lep_41 is shown as SEQ ID NO: 4.

EXAMPLE 8

Purification of Chromosomal DNA from *Torulaspora Delbrueckii*

Cells were prepared by culturing *Torulaspora delbrueckii* JCM 5921 strain on YM medium. Chromosomal DNA was purified from these cells using the method described in Meth. Cell Biol. 22, 39–44 (1975).

EXAMPLE 9

Cloning of the Core Region of the Carbonyl Reductase Gene

Based on the amino acid sequences of the N-terminus and lep_41, sense and antisense primers were synthesized. Each nucleotide sequence is shown in SEQ ID NOs: 5 (TdCr-N1) and 6 (TdCR-41).

Using 50 μL of a reaction solution comprising 50 pmol of both primers TdCR-N1 and TdCR-41, 10 nmol of dNTP, 50 ng of *Torulaspora delbrueckii*-derived chromosomal DNA, Ex-Taq buffer (TAKARA SHUZO CO., Ltd.), and 2 U of Ex-Taq (TAKARA SHUZO CO., Ltd.), 30 cycles of denaturation (94° C., 30 seconds), annealing (51° C., 30 seconds), and elongation (70° C., 20 seconds) were performed using GeneAmp® PCR System 2400 (Applied Biosystems).

A part of the PCR reaction solution was analyzed by agarose gel electrophoresis. As a result, a band that seemed specific could be detected at around 330 bp. The resulting DNA fragment was extracted using phenol/chloroform, precipitated with ethanol and then collected and digested with restriction enzyme EcoRI. The digested DNA was subjected to agarose gel electrophoresis, and the desired band was excised to be purified by Sephaglas Band Prep Kit (Amersham Biosciences).

The resulting DNA fragment was ligated using EcoRI-digested pUC18 (TAKARA SHUZO Co., Ltd.) and a Takara Ligation Kit, and then used to transform the *Escherichia coli* JM109 strain.

The transformants were grown on plates of LB medium (1% Bacto-triptone, 0.5% Bacto-yeast extract, and 1% sodium chloride; hereinafter, abbreviated as LB medium)

comprising ampicillin (50 μg/mL) A number of white colonies were selected by the Blue/White selection method, cultured in liquid LB medium comprising ampicillin, and a plasmid was purified by FlexiPrep (Amersham Biosciences) to obtain pTDR.

Using the purified plasmid, the nucleotide sequence of the inserted DNA was analyzed. PCR was performed using BigDye™ Terminator Cycle Sequencing FS ready Reaction Kit (Applied Biosystems), and the PCR product was analyzed using a DNA sequencer ABI PRISM™ 310 Genetic Analyzer (Applied Biosystems). The determined nucleotide sequence of the core region is shown as SEQ ID NO: 7.

EXAMPLE 10

Analysis of the Nucleotide Sequence at the Periphery of the Core Region of the Carbonyl Reductase Gene

*Torulaspor delbruckii*-derived chromosomal DNA was digested with restriction enzyme BamHI, and each fragment was cyclized at 16° C. overnight by a self-ligation reaction using T4 ligase. Next, using 50 L of a reaction solution comprising 100 pmol of each of the primers TdCR-59 (SEQ ID NO: 8) and TdCR-234 (SEQ ID NO: 9), as well as 25 ng of the cyclized DNA, Ex-Taq buffer (TAKARA SHUZO Co. Ltd.), and 2 U of Ex-Taq (TAKARA SHUZO Co. Ltd.), 30 cycles of denaturation (94° C., 30 seconds), annealing (55° C., 30 seconds), and elongation (72° C., seven minutes) were performed using GeneAmp® PCR System 2400 (Applied Biosystems). A part of the PCR reaction solution was analyzed by agarose gel electrophoresis, and a DNA fragment of about 2000 bp was detected. This DNA fragment was purified using a Sephaglas BandPrep Kit (Amersham Biosciences), and a nucleotide sequence was analyzed by the primer walking method. As a result, the ORF sequence of a carbonyl reductase gene was determined. The DNA sequence thus-determined is shown in SEQ ID NO: 1, and the predicted amino acid sequence is shown in SEQ ID NO: 2. The ORF search was performed using Genetyx-win software (Genetix Corporation).

EXAMPLE 11

Construction of Plasmid pSE-TDX Comprising a Part of the Carbonyl Reductase Gene Tdcr1

The primers Td-ATG1 (SEQ ID NO: 10) and Td-XbaR (SEQ ID NO: 11) were synthesized to clone from the 5'-terminus to an XbaI site of the ORF of the carbonyl reductase gene.

Using 50 μL of a reaction solution comprising 50 pmol of each of the primers Td-ATG1 and Td-XbaR, as well as 10 nmol of dNTP, 50 ng of a chromosomal DNA derived from *Torulaspora delbruectii*, Pfu Turbo DNA polymerase buffer (Stratagene), and 3.75 U of Pfu Turbo DNA polymerase (Stratagene), 30 cycles of denaturation (95° C., two minutes 30 seconds), annealing (55° C., one minute), and elongation (72° C., one minute) were performed using a GeneAmp® PCR System 2400 (Applied Biosystems). The resulting PCR product was designated as Td-PCR1.

The resulting PCR product was collected by extraction with phenol-chloroform and ethanol precipitation. The Td-PCR1 was digested with two restriction enzymes BspHI and XbaI, and subjected to agarose gel electrophoresis. The desired band was excised and then purified by Sephaglas BandPrep Kit (Amersham Biosciences).

Figure 4:
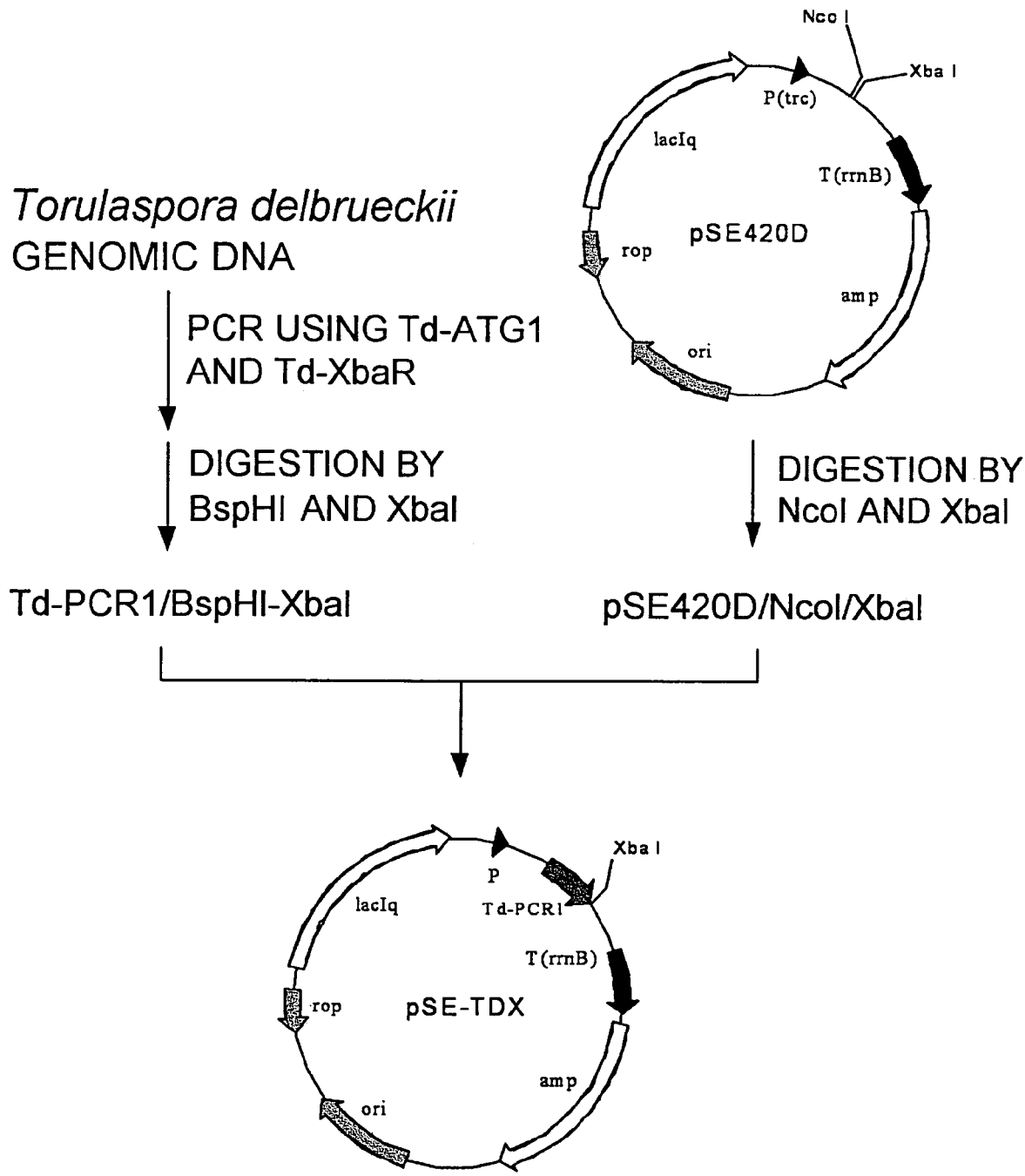
FIG. 4 is a diagram showing the construction of a plasmid (pSE-TDX) into which a part of *Torulaspora delbrueckii*-derived TdCR1 has been introduced.

A Takara Ligation Kit was used to ligate the restriction enzyme-digested Td-PCR1 with the vector pSE420D (JP-A 2000–189170), which had been digested with two restriction enzymes, NcoI and XbaI. *Escherichia coli* JM109 strain was transformed with the ligated plasmid. The transformants were grown on LB medium comprising ampicillin, and the nucleotide sequence of the inserted fragment was analyzed. The obtained plasmid was designated as pSE-TDX. The process of constructing this plasmid is shown in FIG. 4.

EXAMPLE 12

Construction of Plasmid pUC-TDX Comprising a Part of the Carbonyl Reductase Gene TdCR1

Primers Td-XbaF (SEQ ID NO: 12) and Td-TAA1 (SEQ ID NO: 13) were synthesized for cloning from the XbaI site to the 3'-terminus of the ORF of the carbonyl reductase gene.

Using 50 μL of a reaction solution comprising 50 pmol of each of the primers Td-XbaF and Td-TAA1, as well as 10 nmol of dNTP, 50 ng of *Torulaspora delbruectii*-derived chromosomal DNA, Pfu Turbo DNA polymerase buffer (Stratagene), and 3.75 U of Pfu Turbo DNA polymerase (Stratagene), 30 cycles of denaturation (95° C., two minutes 30 seconds), annealing (55° C., one minute), and elongation (72° C., one minute) were performed using a GeneAmp® PCR System 2400 (Applied Biosystems). The resulting PCR product was designated as Td-PCR2.

The resulting PCR product was collected by extraction using phenol-chloroform and ethanol precipitation. The Td-PCR2 was digested with XbaI, and subjected to agarose gel electrophoresis. The desired band was excised and then purified by Sephaglas BandPrep Kit (Amersham Biosciences).

Figure 5:
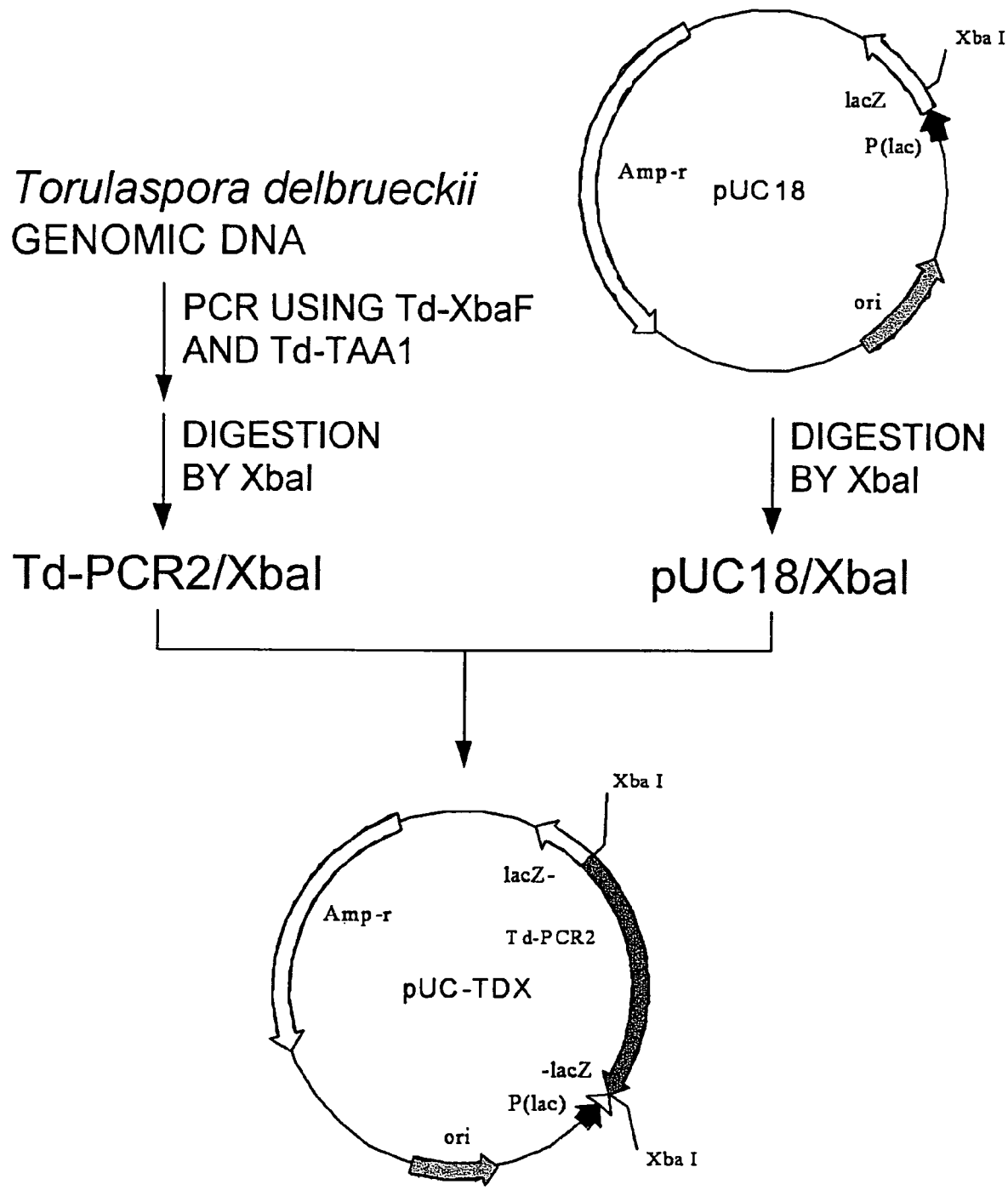
FIG. 5 is a diagram showing the construction of a plasmid (pUC-TDX) into which a part of *Torulaspora delbrueckii*-derived TdCR1 has been introduced.

A Takara Ligation Kit was used to ligate the restriction enzyme-digested Td-PCR2 with the vector pUC18, which had been digested with XbaI. *Escherichia coli* JM109 strain was transformed with the ligated plasmid. The transformants were grown on LB medium comprising ampicillin, and the nucleotide sequence of the inserted fragment was analyzed. The obtained plasmid was designated as PUC-TDX. The process of constructing this plasmid is shown in FIG. 5.

EXAMPLE 13

Construction of Plasmid pSG-TDX Comprising a Part of the Carbonyl Reductase Gene TdCR1

Td-PCR1, the PCR product obtained by the method of Example 11, was collected by extraction with phenol-chloroform and ethanol precipitation. The resulting DNA was digested with two restriction enzymes, BspHI and XbaI, and subjected to agarose gel electrophoresis. The desired band was excised and then purified using a Sephaglas Band Prep Kit (Amersham Biosciences).

Figure 6:
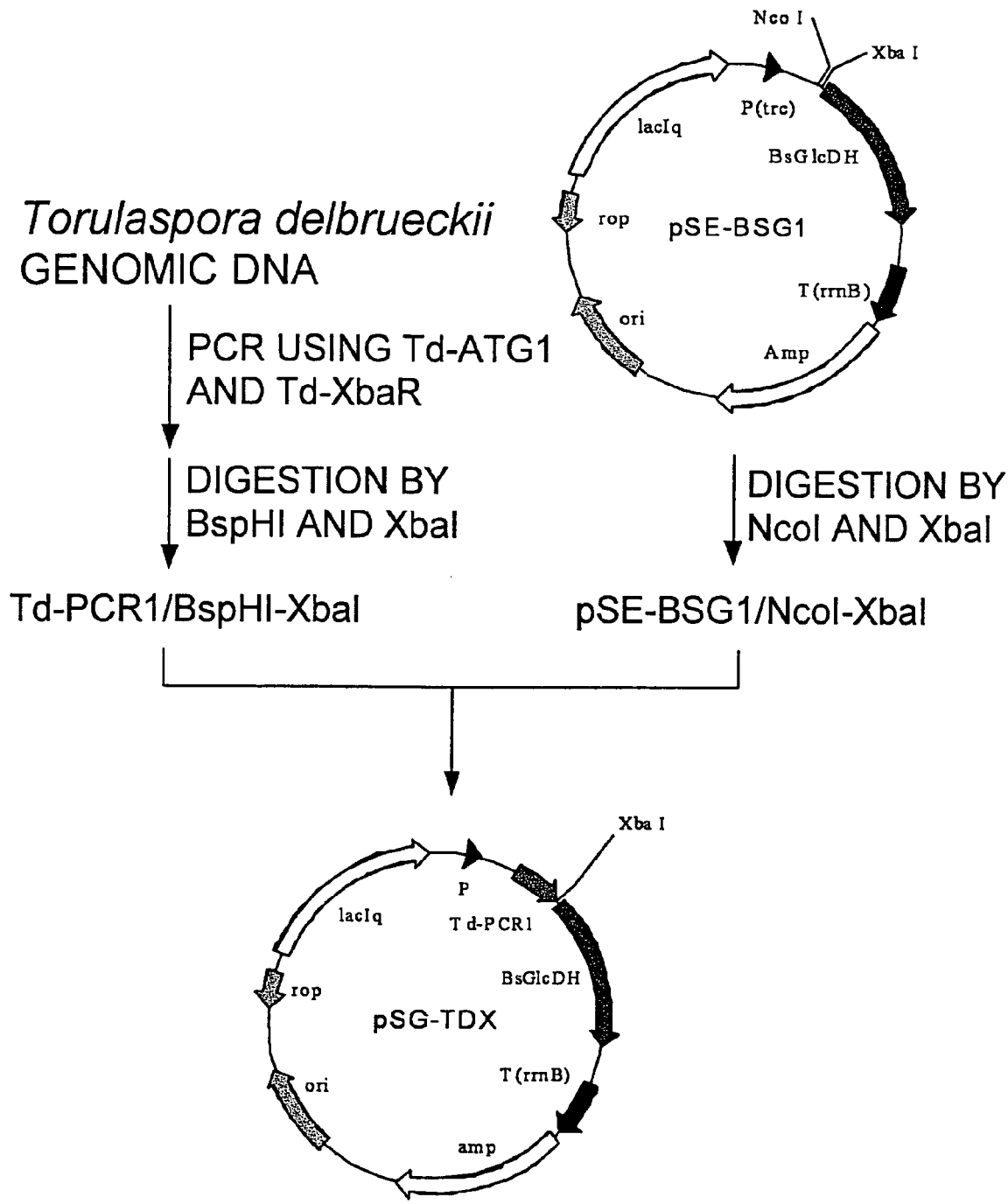
FIG. 6 is a diagram showing the construction of a plasmid (pSG-TDX) into which a part of *Torulaspora delbrueckii*-derived TdCR1 has been introduced.

A Takara Ligation Kit was used to ligate the restriction enzyme-digested Td-PCR1 with the vector pSE-BSG1 (JP-A 2000–189170), which comprises a *Bacillus subtilis*-derived glucose dehydrogenase gene and had been digested with restriction enzymes NcoI and XbaI. *Escherichia coli* JM109 strain was transformed with the ligated plasmid. The transformants were grown on LB medium comprising ampicillin, and the nucleotide sequence of the inserted fragment was analyzed. The obtained plasmid was designated as pSG-TDX. The process of constructing this plasmid is shown in FIG. 6.

EXAMPLE 14

Construction of Plasmid pSE-TDR1 Expressing the Carbonyl Reductase Gene TdCR1

Figure 7:
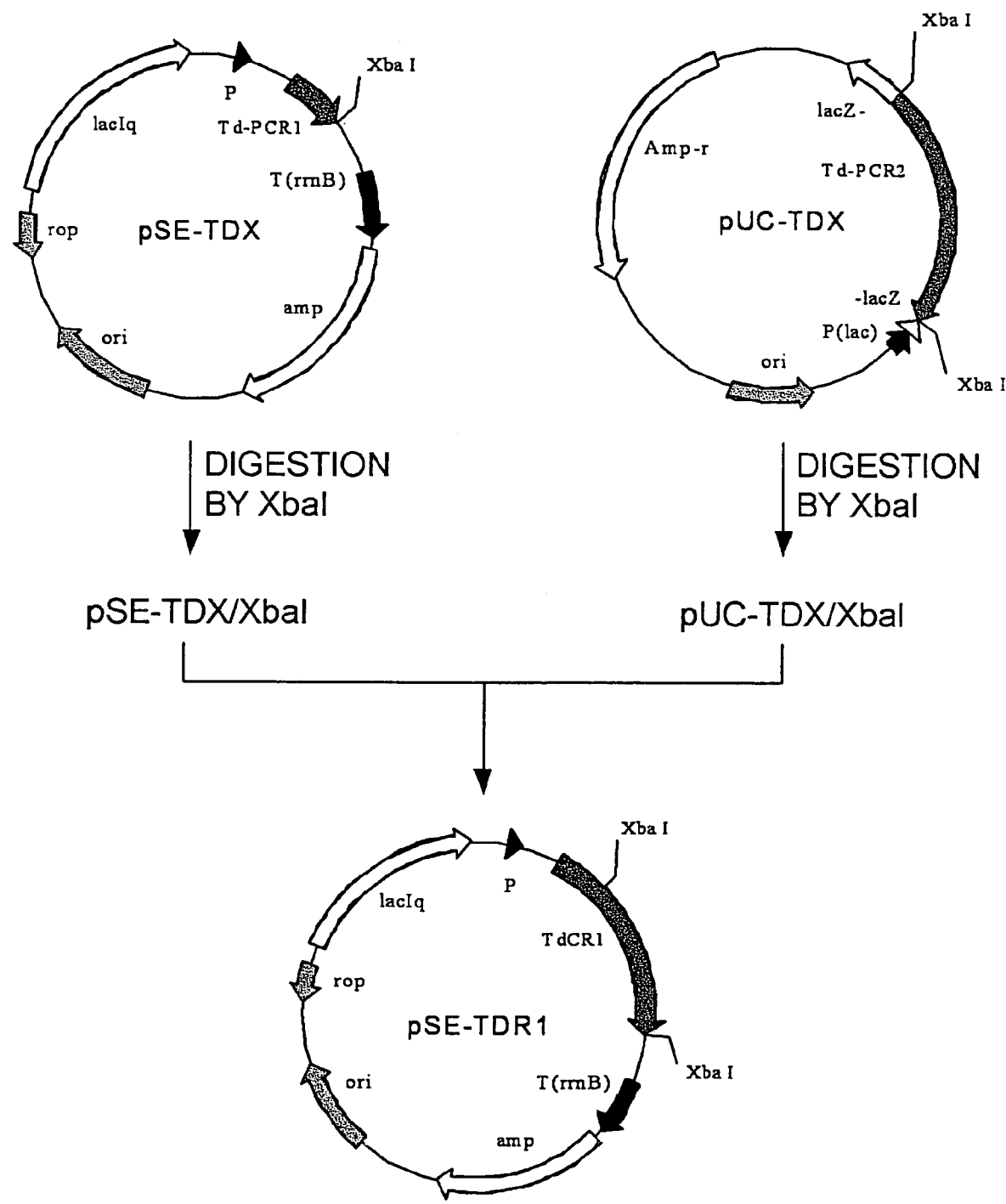
FIG. 7 is a diagram showing the construction of a plasmid (pSE-TDR1) which comprises the full-length TdCR1 gene and can express TdCR1.

The plasmid pUC-TDX obtained in Example 12 was digested using restriction enzyme XbaI, ethanol-precipitated, and then subjected to agarose electrophoresis. A band of about 0.8 kb, comprising part of the TdCR1 gene, was excised. This band was purified by Sephaglas Band Prep (Amersham Biosciences) and collected. A TaKaRa Ligation Kit was used to ligate the resulting DNA fragment with a plasmid pSE-TDX, obtained by digestion with the same restriction enzyme, treatment with alkaline phosphatase, phenol extraction, phenol/chloroform extraction, chloroform extraction, and ethanol precipitation. *Escherichia coli* JM109 strain was transformed with the ligated DNA and cultured on LB medium comprising ampicillin (50 mg/L). A plasmid was purified from the resulting transformants using a Flexi Prep kit. As a result, the plasmid pSE-TDR1, which comprises the full length TdCR1 gene and can express TdCR1, was obtained. The process for constructing this plasmid is shown in FIG. 7.

EXAMPLE 15

Figure 8:
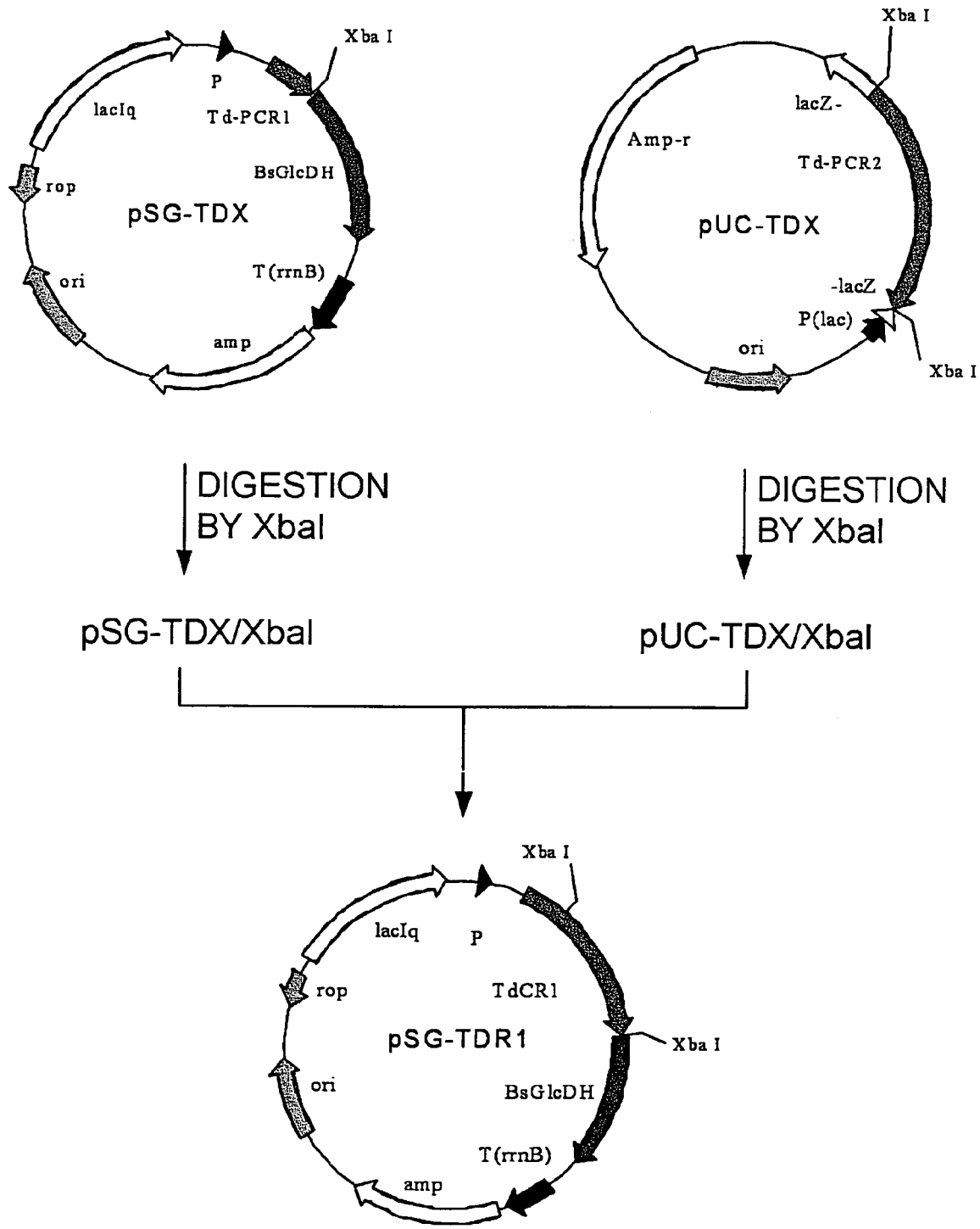
FIG. 8 is a diagram showing the construction of a plasmid (pSG-TDR1) which can coexpress glucose dehydrogenase and TdCR1.

Construction of Plasmid pSG-TDR1, which Coexpresses the Carbonyl Reductase Gene TdCR1 and a *Bacillus Subtilis*-derived Glucose Dehydrogenase Gene The plasmid pUC-TDX obtained in Example 12 was digested with restriction enzyme XbaI, ethanol-precipitated, and then subjected to agarose electrophoresis. A band of about 0.8 kb comprising a part of the TdCR1 gene was excised. This band was purified by Sephaglas Band Prep (Amersham Biosciences) and collected. A TaKaRa Ligation Kit was used to ligate the resulting DNA fragment with plasmid pSG-TDX, obtained by digestion with the same restriction enzyme, treatment with alkaline phosphatase, phenol extraction, phenol/chloroform extraction, chloroform extraction, and ethanol precipitation. *Escherichia coli* JM109 strain was transformed with the ligated DNA and cultured on LB medium comprising ampicillin (50 mg/L). A plasmid was purified with Flexi Prep kit from the resulting transformants. As a result, plasmid pSG-TDR1, which can coexpress the glucose dehydrogenase gene and TdCR1, was obtained. The process for constructing this plasmid is shown in FIG. 8.

EXAMPLE 16

Confirmation of Carbonyl Reductase Activity

*Escherichia coli* JM109 strain transformed with plasmid pSE-TDR1, which expresses carbonyl reductase, and plasmid pSG-TDR1, which coexpresses carbonyl reductase and *Bacillus subtilis*-derived glucose dehydrogenase, was cultured overnight at 30° C. in liquid LB medium containing ampicillin. 0.1 mM IPTG was added, and the strain was further cultured for four hours.

Cells were collected by centrifugation, and then suspended in 50 mM potassium phosphate buffer (pH 6.5) comprising 0.5 M NaCl, 0.02% 2-mercaptoethanol, 2 mM PMSF, and 10% glycerin. Cells were then disrupted by sonication, and centrifuged. The obtained supernatant was used as a cell-free extract. The 3,4-dimethoxyphenylacetone-reducing activity and glucose-dehydrogenating activity of the cell-free extract were measured. The glucose-dehydrogenating activity was measured as follows: Measurements were performed at 30° C. in a reaction solution comprising the enzyme and 100 mM potassium phosphate buffer (pH 6.5), 2.5 mM $NAD^+$, 100 mM glucose. 1 U was defined as the amount of enzyme to catalyze production of 1 mol of NADH per minute under the aforementioned reaction conditions.

Table 3 shows the results of measuring the 3,4-dimethoxyphenylacetone-reducing activity and glucose dehydrogenase activity using each cell-free extract. In all cases, 3,4-dimethoxyphenylacetone-reducing activity was confirmed.

TABLE 3

| Plasmid | 3,4-Dimethoxyphenylacetone reducing activity (mU/mg protein) | Glucose dehydrogenase activity (U/mg protein) |
| --- | --- | --- |
| None | 0 | 0 |
| pSE-TDR1 | 61.6 | 0 |
| pSG-TDR1 | 57.0 | 4.07 |

EXAMPLE 17

Purification of Chromosomal DNA from *Saccharomyces Cerevisiae*

*Saccharomyces cerevisiae* X2180–1B (Yeast Genetic Stock Center) was cultured on YM medium to prepare cells. Purification of chromosomal DNA from these cells was performed by the method described in Meth. Cell Biol. 22, 39–44 (1975).

EXAMPLE 18

Cloning of Carbonyl Reductase Homolog YGL157w

PCR primers YGL1-ATG1 (SEQ ID NO: 14) and YGL1-TAA1 (SEQ ID NO: 15) were synthesized based on a DNA sequence (DDBJ Accession No. Z48618) corresponding to predicted protein YGL157w (SWISS-PROT Accession No. P53111) registered in DDBJ.

Using 50 µL of a reaction solution comprising 25 pmol of each of the primers, as well as 10 nmol of dNTP, 50 ng of *Saccharomyces cerevisiae*-derived chromosomal DNA, Pfu DNA polymerase buffer (Stratagene), and 2 U of Pfu DNA polymerase (Stratagene), PCR of 30 cycles of denaturation (95° C., 45 seconds), annealing (55° C., 30 seconds), and elongation (72° C., one minute 20 seconds) was performed with GeneAmp® PCR System 2400 (Applied Biosystems). As a result, a specific amplification product was obtained.

A TAKARA Ligation Kit was used to ligate the amplification product, which was treated with phenol and then doubly digested with restriction enzymes BspHI and XbaI, with vector pSE420D, which had been doubly digested with restriction enzymes NcoI and XbaI. *Escherichia coli* JM 109 strain was transformed with the ligated DNA, and cultured on the LB medium comprising ampicillin (50 mg/L). FlexiPrep was used to purify a plasmid from the resulting transformants.

Figure 9:
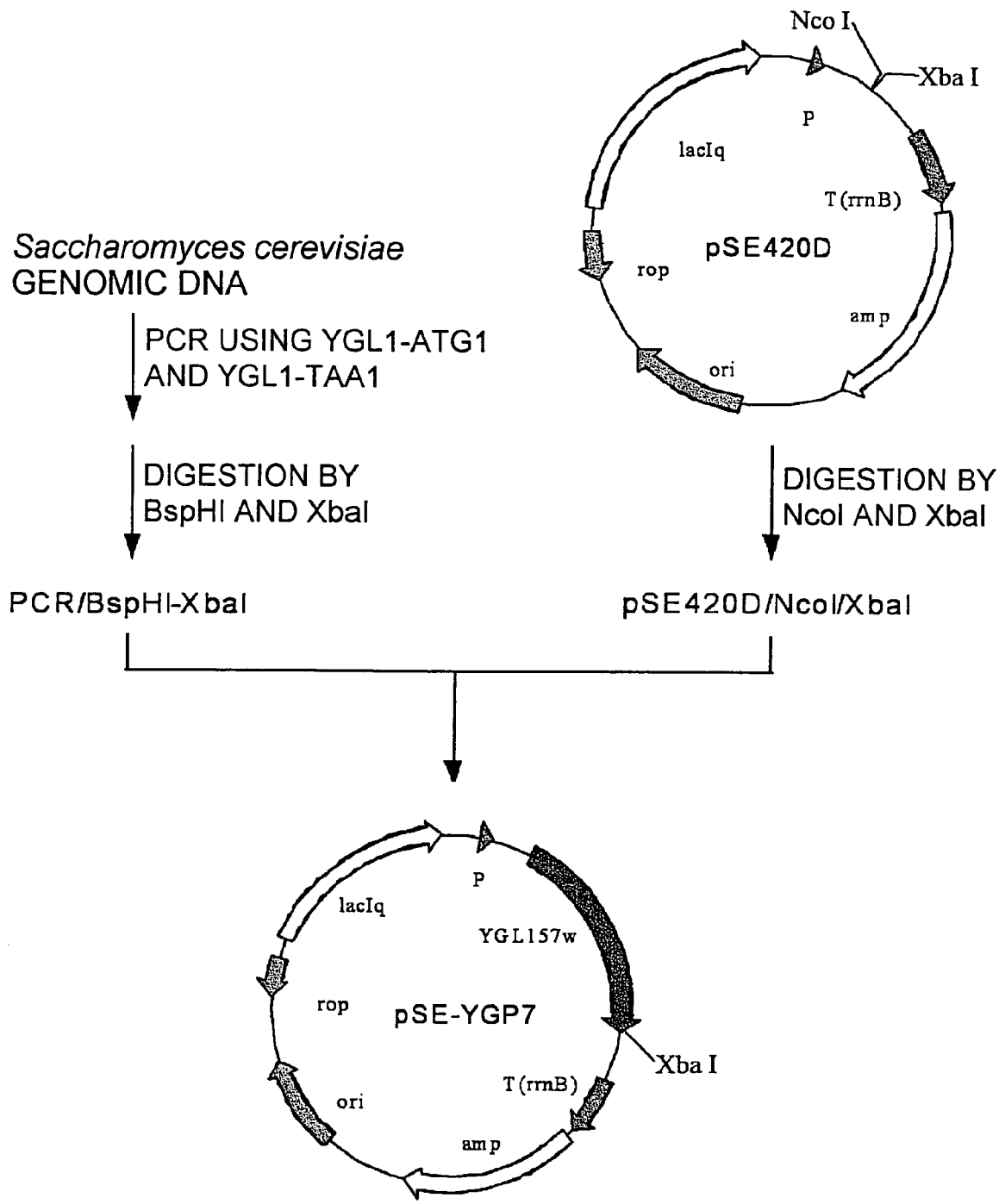
FIG. 9 is a diagram showing the construction of a plasmid (pSE-YGP7) into which a *Saccharomyces cerevisiae*-derived YGL157w gene is introduced. In the plasmid map, P represents a trc promoter, T(rrnB) represents an rrnBT1T2 terminator, amp represents β-lactase gene exhibiting ampicillin resistance, ori represents an origin of replication, rop represents a ROP-protein gene, and laqIq represents a lactose repressor.

The nucleotide sequence of the inserted plasmid DNA was analyzed and SEQ ID NO: 19 shows the resulting sequence. This nucleotide sequence was completely consistent with that registered in DDBJ. The resulting plasmid was designated as pSE-YGP7. The amino acid sequence predicted from the nucleotide sequence of SEQ ID NO: 16 is shown in SEQ ID NO: 17. The process for constructing this plasmid is shown in FIG. 9.

EXAMPLE 19

Figure 10:
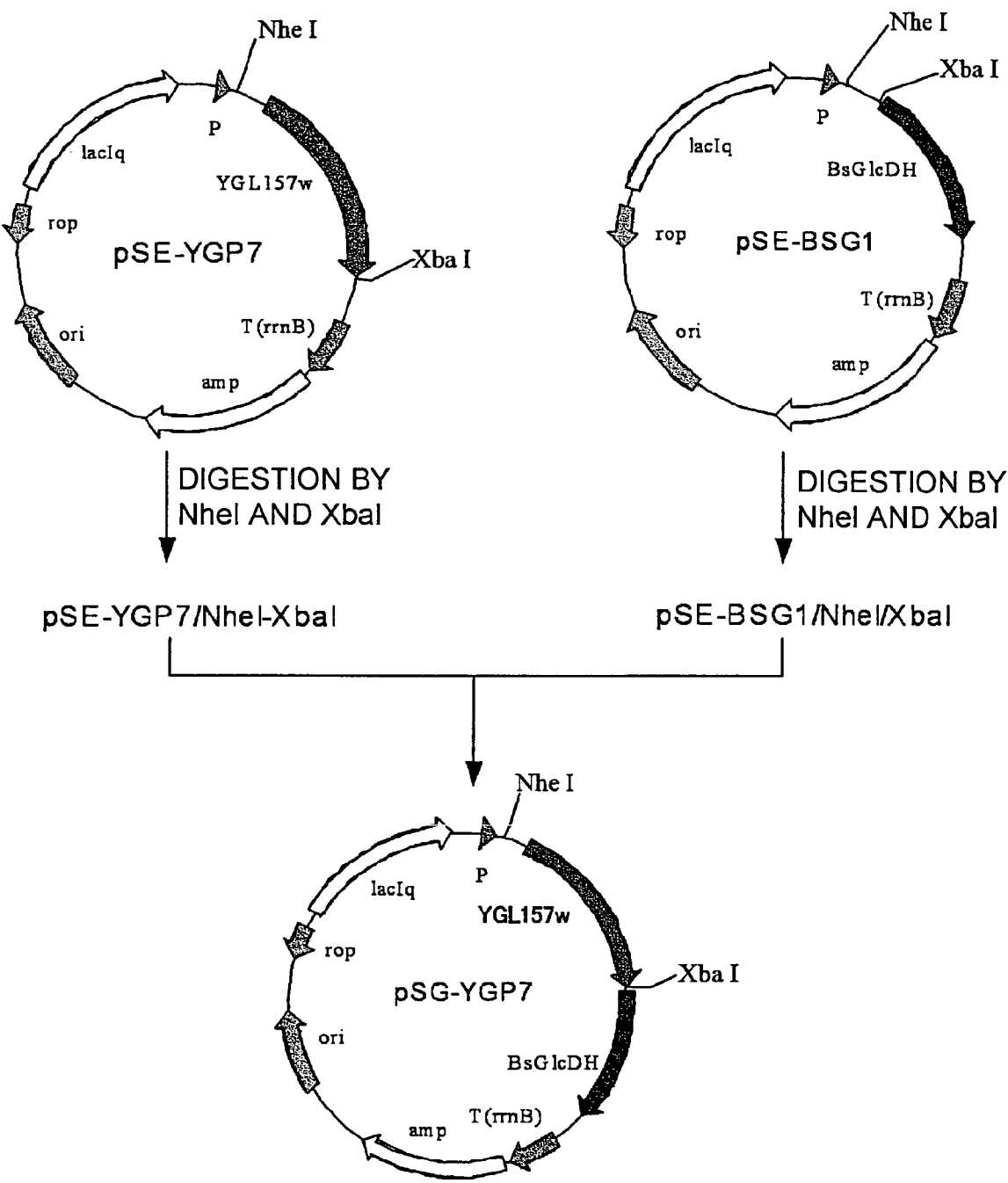
FIG. 10 is a diagram showing the construction of a plasmid (pSG-YGP7) into which a *Saccharomyces cerevisiae*-derived YGL157w gene and a *Bacillus subtilis*-derived glucose dehydrogenase gene have been introduced. In the plasmid map, P represents a trc promoter, T(rrnB) represents an rrnBT1T2 terminator, amp represents a β-lactase gene exhibiting ampicillin resistance, ori represents an origin of replication, rop represents a ROP-protein gene, laqIq represents a lactose repressor, and BsGlcDH represents a *Bacillus subtilis*-derived glucose dehydrogenase gene.

Construction of Plasmid pSG-YGP7, which Coexpresses Carbonyl Reductase Homolog YGL157W and the *Bacillus Subtilis*-derived Glucose Dehydrogenase Gene The plasmid pSE-BSG1 (JPA 2000–374593), which comprised a *Bacillus subtilis*-derived glucose dehydrogenase gene, was doubly digested with two restriction enzymes, NheI and XbaI. A Takara Ligation Kit was then used to ligate the plasmid with a DNA fragment comprising a YGL157w gene excised from pSE-YGP7 using the same enzymes. *Escherichia coli* JM109 strain was transformed with the ligated DNA, cultured on LB medium comprising ampicillin (50 mg/L), and FlexiPrep was used to purify from the resulting transformants the plasmid pSG-YGP7, which is capable of coexpressing glucose dehydrogenase and YGL157w. The process for constructing this plasmid is shown in FIG. 10.

EXAMPLE 20

Cloning of Carbonyl Reductase Homolog YGL039W

PCR primers YGL2-ATG2 (SEQ ID NO: 18) and YGL2-TAA2 (SEQ ID NO: 19) were synthesized based on the DNA sequence (DDBJ Accession No. Z72561) corresponding to the predicted protein YGL039w (SWISS-PROT Accession No. P53183), registered in DDBJ.

Using 50 µL of a reaction solution comprising 25 pmol of each of the primers, as well as 10 nmol of dNTP, 50 ng of *Saccharomyces cerevisiae*-derived chromosomal DNA, Pfu DNA polymerase buffer (Stratagene), and 2 U of Pfu DNA polymerase (Stratagene), PCR of 30 cycles of denaturation (95° C., 45 seconds), annealing (50° C., 30 seconds), and elongation (720C, one minute 15 seconds) was performed with GeneAmp® PCR System 2400 (Applied Biosystems). As a result, a specific amplification product was obtained.

Figure 11:
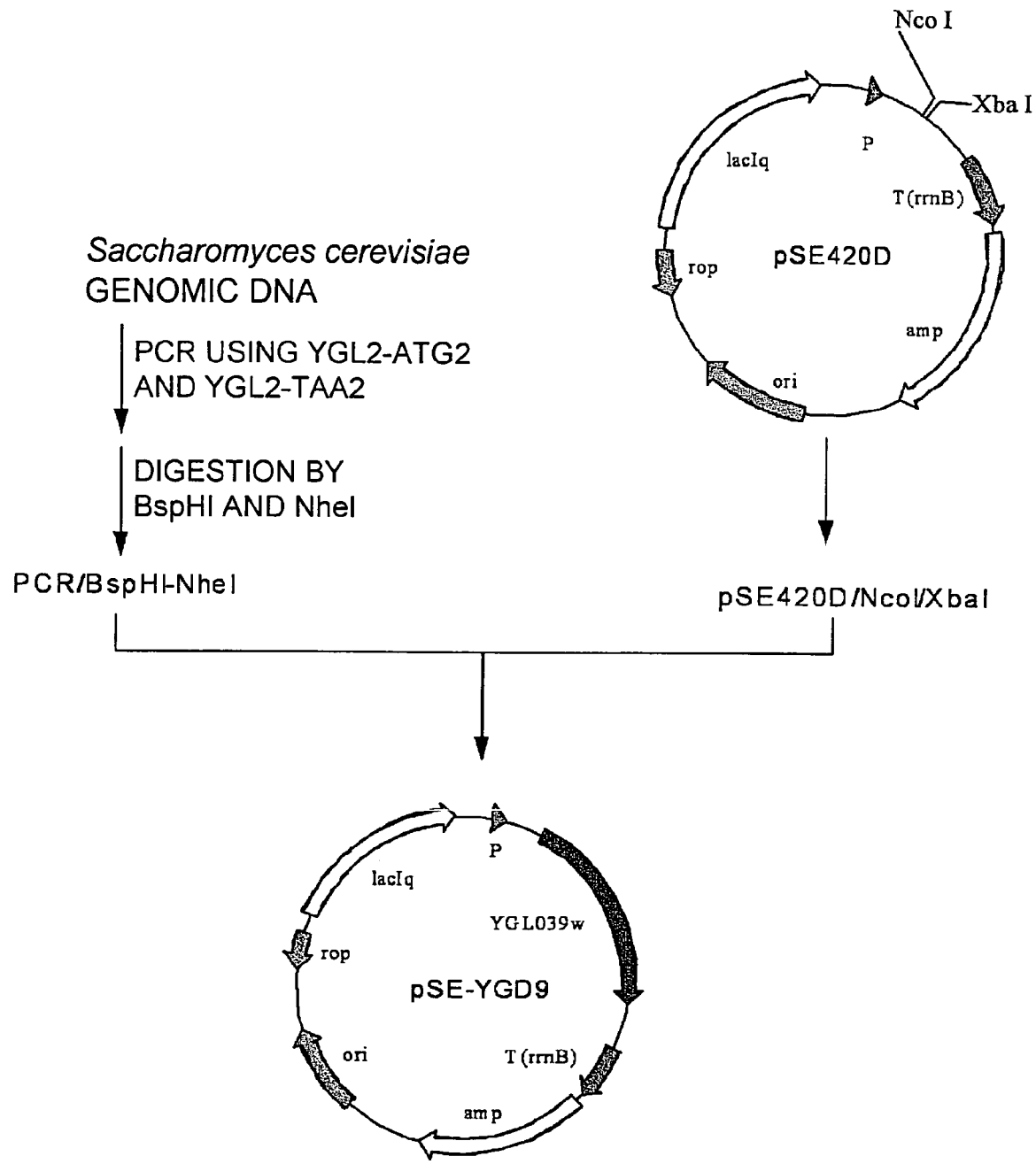
FIG. 11 is a diagram showing the construction of a plasmid (pSE-YGD9) into which a *Saccharomyces cerevisiae*-derived YGL039w gene has been introduced. In the plasmid map, P represents a trc promoter, T (rrnB) represents an rrnBT1T2 terminator, amp represents a β-lactase gene exhibiting ampicillin resistance, ori represents an origin of replication, rop represents a ROP-protein gene, and laqIq represents a lactose repressor.

The amplification product was treated with phenol, doubly digested with restriction enzymes BspHI and NheI, and ligated using a TAKARA Ligation Kit with vector pSE420D, which had been doubly digested with restriction enzymes NcoI and XbaI. *Escherichia coli* JM109 strain was transformed with the ligated DNA, and cultured on LB medium comprising ampicillin (50 mg/L). Flexi Prep was used to purify a plasmid from the resulting transformants. The nucleotide sequence of the inserted plasmid DNA was analyzed, and the resulting sequence is shown in SEQ ID NO: 20. This nucleotide sequence was completely consistent with that registered in DDBJ. The resulting plasmid was designated as pSE-YGD9. The amino acid sequence predicted from the nucleotide sequence of SEQ ID NO: 20 is shown in SEQ ID NO: 21. The process for constructing this plasmid is shown in FIG. 11.

EXAMPLE 21

Construction of Plasmid pSG-YGD9, which can Coexpress Carbonyl Reductase Homolog YGL039w and *Bacillus subtilis*-derived Glucose Dehydrogenase Gene pSE-YGD9 was doubly digested with two restriction enzymes, EcoRI and HindIII. A Takara Ligation Kit was then used to ligate the product with a DNA fragment comprising a glucose dehydrogenase gene, which was excised using the same enzymes from plasmid pSE-BSG1 (JP-A 2000–374593), which comprises the *Bacillus subtilis*-derived glucose dehydrogenase gene.

Figure 12:
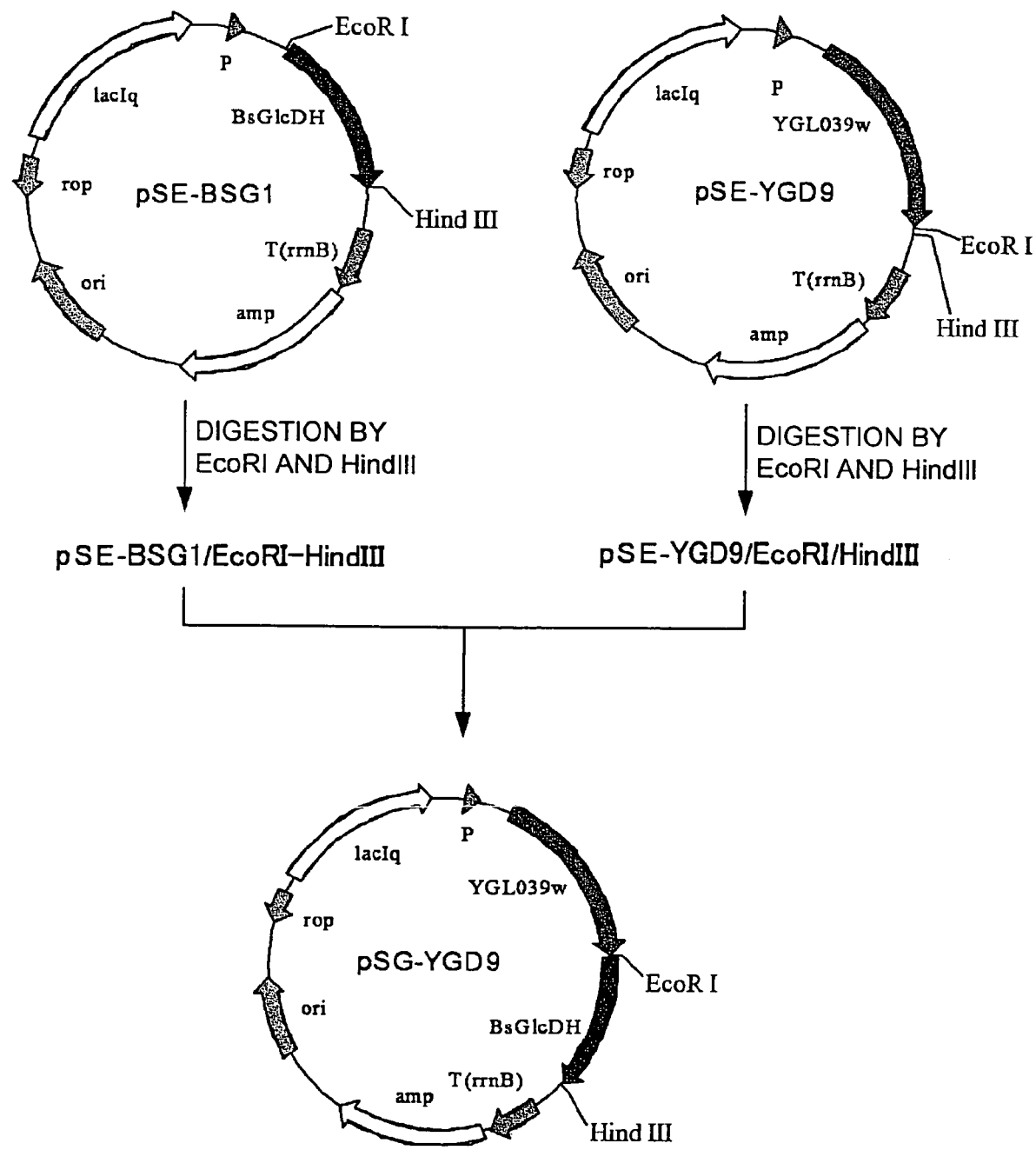
FIG. 12 is a diagram showing the construction of a plasmid (pSG-YGD9) into which a *Saccharomyces cereisiae*-derived YGL039w gene and a *Bacillus subtilis*-derived glucose dehydrogenase gene have been introduced. In the plasmid map, P represents a trc promoter, T(rrnB) represents an rrnBT1T2 terminator, amp represents a β-lactase gene exhibiting ampicillin resistance, ori represents an origin of replication, rop represents a ROP-protein gene, laqIq represents a lactose repressor, and BsGlcDH represents a *Bacillus subtilis*-derived glucose dehydrogenase gene.

*Escherichia coli* JM109 strain was transformed with the ligated DNA, cultured on LB medium comprising ampicillin (50 mg/L), and Flexi Prep was used to purify from the resulting transformants the plasmid pSG-YGP9, which is capable of coexpressing glucose dehydrogenase and YGL039w. The process for constructing this plasmid is shown in FIG. 12.

EXAMPLE 22

Cloning of the Carbonyl Reductase Homolog YDR541c

PCR primers YDR-ATG1 (SEQ ID NO: 18) and YDR-TAA1 (SEQ ID NO: 23) were synthesized based on the DNA sequence (DDBJ Accession No. Z48239) corresponding to the predicted protein YDR541c (SWISS-PROT Accession No. U43834–5), registered in DDBJ.

Using 50 µL of a reaction solution comprising 25 pmol of each of the primers, as well as 10 nmol of dNTP, 50 ng of *Saccharomyces cerevisiae*-derived chromosomal DNA, Pfu DNA polymerase buffer (Stratagene), and 2 U of Pfu DNA polymerase (Stratagene), PCR of 30 cycles of denaturation (95° C., 45 seconds), annealing (52° C., 30 seconds), and elongation (72° C., one minute 20 seconds) was performed with GeneAmpe® PCR System 2400 (Applied Biosystems). As a result, a specific amplification product was obtained.

Figure 13:
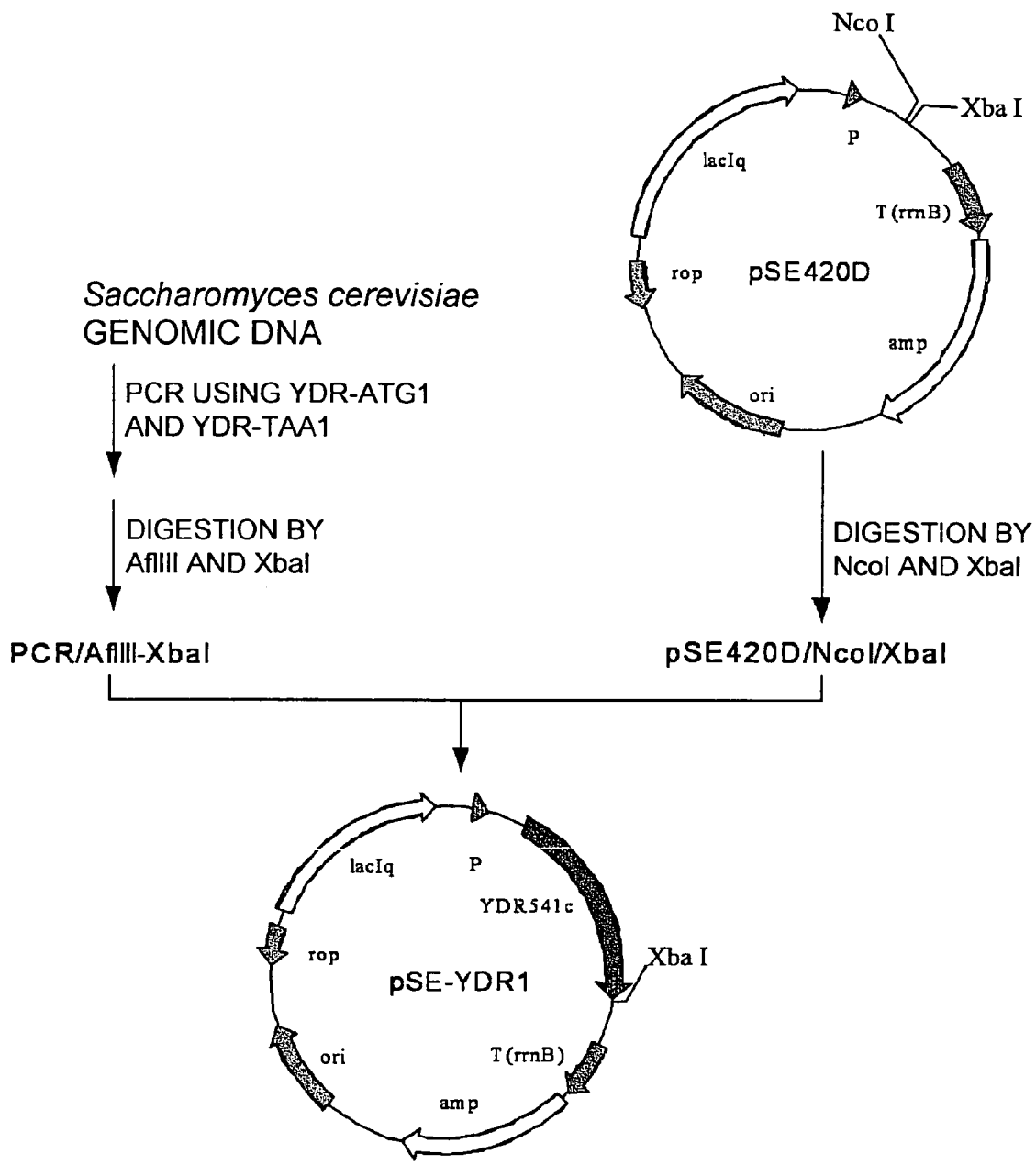
FIG. 13 is a diagram showing the construction of a plasmid (pSE-YDR1) into which a *Saccharomyces cerevisiae*-derived YDR541c gene has been introduced. In the plasmid map, P represents a trc promoter, T (rrnB) represents an rrnBT1T2 terminator, amp represents a β-lactase gene exhibiting ampicillin resistance, ori represents an origin of replication, rop represents a ROP-protein gene, and laqIq represents a lactose repressor.

The amplification product was treated with phenol, doubly digested with restriction enzymes AflIII and XbaI, and ligated using a TAKARA Ligation Kit with vector pSE420D, which had been doubly digested with restriction enzymes NcoI and XbaI. *Escherichia coli* JM 109 strain was transformed with the ligated DNA, and cultured on LB medium comprising ampicillin (50 mg/L). Flexi Prep was used to purify a plasmid from the resulting transformants. The nucleotide sequence of the inserted plasmid DNA was analyzed, and the resulting sequence is shown in SEQ ID NO: 27. This nucleotide sequence was completely consistent with that registered in DDBJ. The resulting plasmid was designated as pSE-YDR1. The amino acid sequence predicted from the nucleotide sequence of SEQ ID NO: 24 is shown in SEQ ID NO: 25. The process for constructing this plasmid is shown in FIG. 13.

EXAMPLE 23

Construction of Plasmid pSG-YGD7, which can Coexpress Carbonyl Reductase Homolog YDR541c and *Bacillus Subtilis*-derived Glucose Dehydrogenase Gene pSE-YDR1 was doubly digested with two restriction enzymes EcoRI and HindIII. A Takara Ligation Kit was then used to ligate the product with a DNA fragment that comprised a glucose dehydrogenase gene excised using the same enzymes from plasmid pSE-BSG1 (JP-A2000-374593), which comprised the *Bacillus subtilis*-derived glucose dehydrogenase gene.

Figure 14:
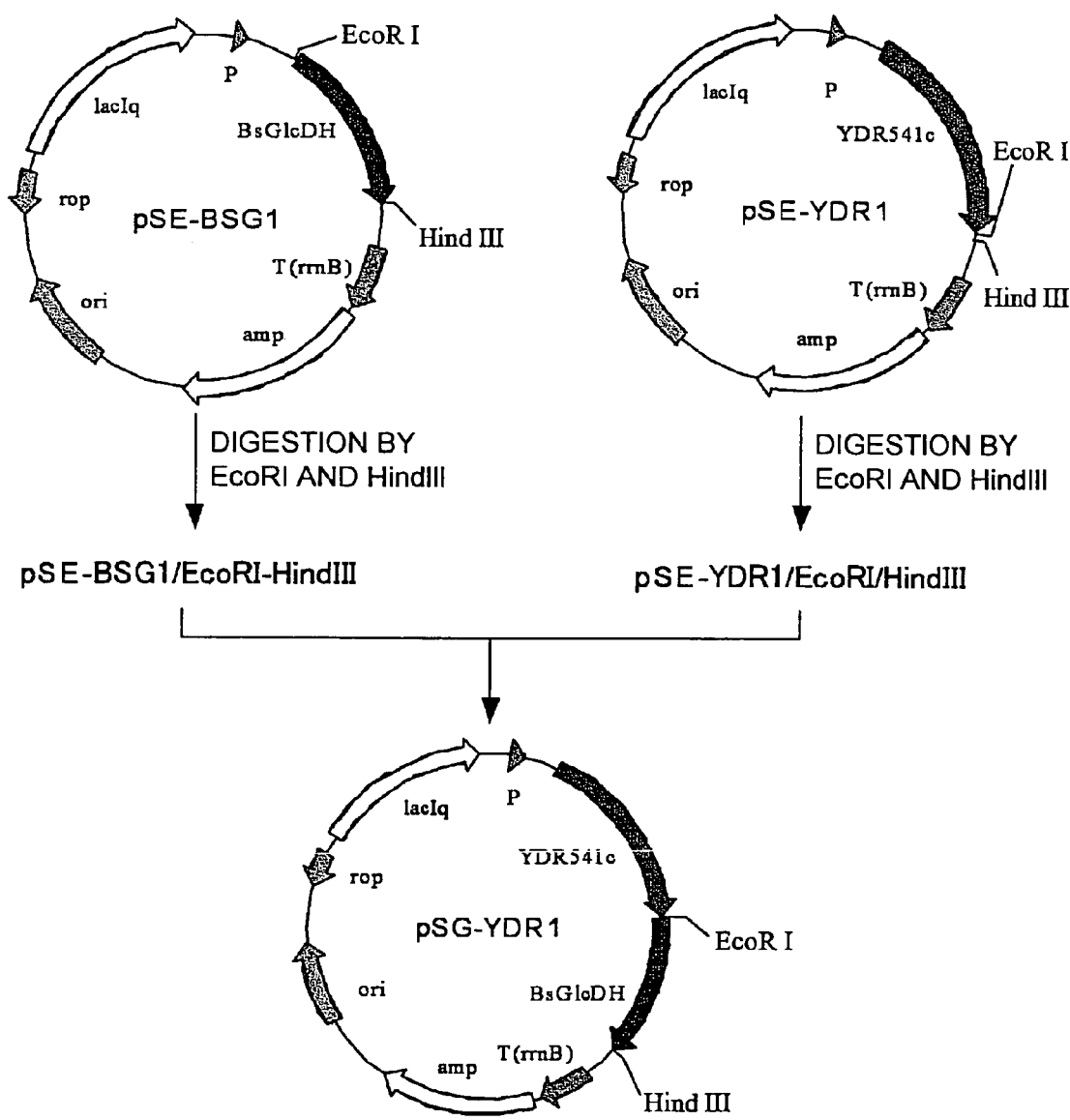
FIG. 14 is a diagram showing the construction of a plasmid (pSG-YDR1) into which a *Saccharomyces cerevisiae*-derived YDR541c gene and a *Bacillus subtilis*-derived glucose dehydrogenase gene have been introduced. In the plasmid map, P represents a trc promoter, T(rrnB) represents an rrnBT1T2 terminator, amp represents a α-lactase gene exhibiting ampicillin resistance, ori represents an origin of replication, rop represents a ROP-protein gene, laqIq represents a lactose repressor, and BsClcDH represents a *Bacillus subtilis*-derived glucose dehydrogenase gene.

*Escherichia coli* JM109 strain was transformed with the ligated DNA, cultured on LB medium comprising ampicillin (50 mg/L), and Flexi Prep was used to purify from the resulting transformants the plasmid pSG-YDR1, which is capable of coexpressing glucose dehydrogenase and YDR541c. The process for constructing this plasmid is shown in FIG. 14.

EXAMPLE 24

Confirmation of the Activity of Carbonyl Reductase Homologs YGL157w, YGL039w, and YDR541c

*Escherichia coli* JM109+strains comprising pSE-YGP7, pSE-YGD9, pSE-YDR1, pSG-YGP7, pSG-YGD9, or pSG-YDR1 were cultured on LB medium comprising ampicillin, induced with 0.1 mM IPTG for four hours, and then centrifuged to collect the cells.

Each of these cell samples was suspended in a cell lysis solution (50 mM KPB pH 8.0, 1 mM EDTA, 0.02% 2-mercaptoethanol, 2 mM PMSF, 10% Glycerol). The cells were ruptured by sonication and then centrifuged to obtain the supernatant, which was used as a cell-free extract.

3,4-dimethoxyphenylacetone-reducing activity was measured using each cell-free extract, and the results are shown in Table 4. YGL157w (pSE-YGP7 and pSG-YGP7), YGL039w (pSE-YGD9 and pSG-YGD9), and YDR541c (pSE-YDR1 and pSG-YDR1) were all confirmed to comprise 3,4-dimethoxyphenylacetone reductase activity.

TABLE 4

| Plasmid | 3,4-Dimethoxyphenylacetone reducing activity (mU/mg protein) | Glucose dehydrogenating activity (mU/mg protein) |
|---|---|---|
| None | 0.0 | 0.0 |
| pSE-YGP7 | 39.0 | 0.0 |
| pSG-YGP7 | 6.85 | 2320 |
| pSE-YGD9 | 19.1 | 0.0 |
| pSG-YGD9 | 20.0 | 1340 |
| pSE-YDR1 | 21.0 | 0.0 |
| pSG-YDR1 | 30.0 | 30.0 |

EXAMPLE 25

Synthesis of (S)-1-(3,4-dimethoxyphenyl)-2-propanol by Carbonyl Reductase Homologs YGL157w, YGL039w, and YDR541c To prepare crude enzyme solution for enzyme reaction, the crude enzyme solution prepared in Example 18 was concentrated ten-folds using a UF membrane. This solution was reacted overnight at 25° C. in 1 mL of a reaction solution comprising 200 mM potassium phosphate buffer (pH 6.5), 1 mM $NADP^+$, 2 U glucose dehydrogenase (Wako Pure Chemical Industries, Ltd.), 250 mM glucose, 0.2 U homolog enzyme, and 50 mM 3,4-dimethoxyphenylacetone. Optical purity was measured and the produced (S)-1-(3,4-dimethoxyphenyl)-2-propanol was quantified as in Example 6. As a result, YGL157w (pSE-YGP7) produced 93.7% ee (S)-1-(3,4-dimethoxyphenyl)-2-propanol at a yield of 66%, YGL039w (pSE-YGD9) produced 93.6% ee at a yield of 94%, and YDR541c (pSE-YDR1) produced 94.8% ee at a yield of 6%.

What is claimed is:

1. An isolated and purified polynucleotide comprising the nucleotide sequence of SEQ ID NO: 1 or encoding a protein comprising the amino acid sequence of SEQ ID NO: 2.

2. An isolated and purified protein encoded by the polynucleotide of claim 1.

3. A recombinant vector, which comprises the polynucleotide of claim 1.

4. The recombinant vector of claim 3, which further comprises a dehydrogenase gene for regenerating a coenzyme.

5. A transformant, comprising a microorganism, which is transformed with the polynucleotide of claim 1.

6. A method for producing an optically active alcohol, which comprises reacting the protein of claim 2 with a ketone.

7. A method for producing (S)-1-(3,4-dimethoxyphenyl)-2-propanol, which comprises reacting the protein of claim 2 with 3,4-dimethoxyphenylacetone.

8. The transformant of claim 5, wherein the microorganism is selected from the group consisting of bacteria, Actinomycetes, yeast and fungi.

* * * * *